(12) United States Patent
Tajima et al.

(10) Patent No.: US 9,469,844 B2
(45) Date of Patent: *Oct. 18, 2016

(54) FLAVIN-BOUND GLUCOSE DEHYDROGENASES, A METHOD FOR PRODUCING A FLAVIN-BOUND GLUCOSE DEHYDROGENASE, AND YEAST TRANSFORMANT USED FOR THE SAME

(75) Inventors: Ryoko Tajima, Noda (JP); Atsushi Ichiyanagi, Noda (JP); Kozo Hirokawa, Noda (JP); Masanobu Yuzuki, Noda (JP)

(73) Assignee: KIKKOMAN CORPORATION, Noda-Shi, Chiba ( * ) Notice: Subject to any disclaimer, the term of this patent is extended or adjusted under 35 U.S.C. 154(b) by 360 days.

This patent is subject to a terminal disclaimer.

(21) Appl. No.: 13/991,087

(22) PCT Filed: Nov. 30, 2011

(86) PCT No.: PCT/JP2011/077607
§ 371 (c)(1),
(2), (4) Date: May 31, 2013

(87) PCT Pub. No.: WO2012/073986
PCT Pub. Date: Jun. 7, 2012

(65) Prior Publication Data
US 2014/0057331 A1    Feb. 27, 2014

(30) Foreign Application Priority Data
Dec. 2, 2010 (JP) .................. 2010-269056

(51) Int. Cl.
| C12N 9/04 | (2006.01) |
| C12N 1/14 | (2006.01) |
| C12P 21/06 | (2006.01) |
| C12P 21/04 | (2006.01) |
| C07H 21/04 | (2006.01) |
| C12N 15/00 | (2006.01) |
| C12N 1/20 | (2006.01) |
| C12N 15/81 | (2006.01) |
| C12N 1/16 | (2006.01) |

(52) U.S. Cl.
CPC .............. C12N 9/0006 (2013.01); C12N 1/16 (2013.01); C12N 15/81 (2013.01); C12Y 101/9901 (2013.01)

(58) Field of Classification Search
CPC ............................ C12N 9/0006; C12N 15/81
See application file for complete search history.

(56) References Cited

U.S. PATENT DOCUMENTS

| 7,514,250 | B2 * | 4/2009 | Omura | C12N 9/0004 435/14 |
| 7,741,100 | B2 | 6/2010 | Kitabayashi et al. | |
| 8,445,246 | B2 | 5/2013 | Tajima et al. | |
| 9,074,239 | B2 * | 7/2015 | Tajima et al. | |
| 2006/0063217 | A1 | 3/2006 | Omura et al. | |
| 2008/0003628 | A1 | 1/2008 | Kitabayashi et al. | |
| 2008/0090278 | A1 | 4/2008 | Kitabayashi et al. | |
| 2009/0176262 | A1 | 7/2009 | Omura et al. | |
| 2009/0181408 | A1 | 7/2009 | Tanaka et al. | |
| 2009/0317848 | A1 | 12/2009 | Kawaminami et al. | |
| 2010/0297743 | A1 | 11/2010 | Omura et al. | |
| 2010/0323378 | A1 | 12/2010 | Honda et al. | |
| 2011/0045513 | A1 | 2/2011 | Takenaka et al. | |
| 2011/0053194 | A1 | 3/2011 | Yuuki et al. | |
| 2011/0318810 | A1 * | 12/2011 | Tajima et al. ............... 435/190 |
| 2013/0168263 | A1 | 7/2013 | Sode et al. | |
| 2013/0309750 | A1 | 11/2013 | Tajima et al. | |
| 2015/0064733 | A1 | 3/2015 | Duefel et al. | |

FOREIGN PATENT DOCUMENTS

| EP | 1862543 A1 | 12/2007 |
| EP | 2241621 A1 | 10/2010 |
| EP | 2508600 A | 10/2010 |
| JP | 2005176602 A | 7/2005 |
| JP | 2007-289148 A | 11/2007 |
| JP | 2007/289148 A | 11/2007 |
| JP | 2008-154574 A | 7/2008 |
| JP | 2008/237210 A | 10/2008 |
| JP | 2008-237210 A | 10/2008 |
| JP | 2010-035448 A | 2/2010 |
| JP | 4494978 B2 | 6/2010 |
| JP | 2010-269056 A | 12/2010 |

(Continued)

OTHER PUBLICATIONS

Branden et al. Introduction to Protein Structure, Garland Publishing Inc., New York, p. 247, 1991.*
U.S. Appl. No. 14/124,559, filed Dec. 6, 2013, First Named Inventor: Ryoko Tajima.
Yamaoka et al., Site Directed Mutagenesis Studies of FAD-dependent Glucose Dehydrogenase Catalytic Subunit of Burkholderia Cepacia, Biotechnol. Lett., Nov. 30, 2008(11), pp. 1967-1972.
U.S. Appl. No. 14/355,326, filed Apr. 30, 2014.
U.S. Appl. No. 13/991,031, filed May 31, 2013.

(Continued)

Primary Examiner — Yong Pak
(74) Attorney, Agent, or Firm — Holtz, Holtz & Volek PC

(57) ABSTRACT

A heat-resistant flavin-bound glucose dehydrogenase having a high substrate specificity for D-glucose, an method for producing the same, and a transformant used for the same. A flavin-bound glucose dehydrogenase gene encoding a flavin-bound glucose dehydrogenase derived from *Mucor* is introduced into yeast, *Zygosaccharomyces*, to obtain a transformant. Subsequently, the yeast transformant is cultured to obtain a flavin-bound glucose dehydrogenase from the culture. The heat-resistant flavin-bound glucose dehydrogenase is less susceptible to the effects of dissolved oxygen and allows accurate measurement of glucose even in the presence of sugar compounds other than glucose in a sample.

10 Claims, 10 Drawing Sheets

(56) References Cited

FOREIGN PATENT DOCUMENTS

| JP | 4648993 B2 | 3/2011 |
|---|---|---|
| JP | 2011-115156 A | 6/2011 |
| JP | 2011139677 A | 7/2011 |
| JP | 2012055229 A | 3/2012 |
| JP | 2012191882 A | 10/2012 |
| WO | WO 2004/058958 A1 | 7/2004 |
| WO | WO 2006101239 A1 | 9/2006 |
| WO | WO 2007/139013 A1 | 6/2007 |
| WO | WO 2009/069381 A1 | 6/2009 |
| WO | WO 2009/084616 A1 | 7/2009 |
| WO | WO 2010/140431 A1 | 12/2010 |
| WO | WO 2011/004654 A1 | 1/2011 |
| WO | WO 2011/068050 A1 | 6/2011 |
| WO | 2012001976 A1 | 1/2012 |
| WO | 2013164477 A1 | 11/2013 |

OTHER PUBLICATIONS

English-language International Preliminary Report on Patentability and Written Opinion of the International Searching Authority, dated Jun. 13, 2013 for International Application PCT/JP2011/077607 filed Nov. 30, 2011; Applicants: Kikkoman Corporation et al.
*Pharmaceuticals and Medical Devices Safety Information*, No. 206 (Oct. 2004) with English translation.
Tchan-Gi Bak et al., "Studies on the Glucose Dehydrogenase *Aspergillus oryzae*", Biochim. Biophys. Acta, 139, pp. 256-276 (1967).
Tchan-Gi Bak, "Studies on the Glucose Dehydrogenase *Aspergillus oryzae*", Biochim. Biophys. Acta, 139, pp. 277-293 (1967).
Tchan-Gi Bak, "Studies on the Glucose Dehydrogenase *Aspergillus oryzae*", Biochim. Biophys. Acta, 139, pp. 317-327 (1967).
Tchan-Gi Bak et al., "Studies on the Glucose Dehydrogenase *Aspergillus oryzae*", Biochim. Biophys. Acta, 139, pp. 328-335 (1967).
English-language International Search Report for PCT/JP2011/077607 mailed Mar. 6, 2012.
Glucose dehydrogenase [Flavin] (2005, updated) http://www.uniprot.org/uniprot/P18172, pp. 1-9.
SEQ-Align (2015) pp. 1-2.
SEQ-Align III (2015) pp. 1-2.
SEQ-Align II (2015) pp. 1-2.
Chica, et al., "Semi-rational approaches to engineering enzyme activity: combining the benefits of directed evolution and rational design", Current Opinion in Biotechnology; Jul. 1, 2005; 16:378-384.
Sen, et al., "Developments in Directed Evolution for Improving Enzyme Functions", Appl Biochem Biotechnol; Aug. 18, 2007; 143:212-223.
Krasney, et al., "Evolution of the Glucose Dehydrogenase Gene in *Drosophila*", Mol. Biol. Evol., vol. 7, 1990, pp. 155-177.
U.S. Appl. No. 15/108,528; First Named Inventor: Yasuko Araki; Title: "Flavin-Binding Glucose Dehydrogenase Exhibiting Improved Heat Stability"; Filed: Jun. 27, 2016.

\* cited by examiner (A)

(B)

(C)

FLAVIN-BOUND GLUCOSE DEHYDROGENASES, A METHOD FOR PRODUCING A FLAVIN-BOUND GLUCOSE DEHYDROGENASE, AND YEAST TRANSFORMANT USED FOR THE SAME

CROSS-REFERENCE TO RELATED APPLICATION

This application is the United States national phase application of International Application PCT/JP2011/077607 filed Nov. 30, 2011.

TECHNICAL FIELD

The invention relates to a novel flavin-bound glucose dehydrogenase, a method for producing a flavin-bound glucose dehydrogenase, and yeast transformant used for the same.

BACKGROUND ART

Blood glucose levels (blood sugar levels) are an important marker of diabetes. An SMBG (self-monitoring of blood glucose) device using an electrochemical biosensor is widely used for managing blood glucose levels in patients with diabetes. Enzymes that catalyze glucose as a substrate, such as glucose oxidase (GOD), have conventionally been used for biosensors employed in SMBG devices. However, GOD is characterized by the use of oxygen as an electron acceptor. Thus, dissolved oxygen in a sample may influence the measurement in SMBG devices using GOD, precluding accurate measurement.

Other enzymes that use glucose as a substrate, but do not use oxygen as an electron acceptor include various glucose dehydrogenases (GDHs). Specifically, GDH (NAD (P)-GDH) that uses nicotinamide dinucleotide (NAD) or nicotinamide dinucleotide phosphate (NADP) as a coenzyme and GDH (PQQ-GDH) that uses pyrroloquinoline quinone (PQQ) as a coenzyme were found, and have been used for the biosensors of SMBG devices. However, NAD (P)-GDH has a problem that the enzyme is unstable and requires the addition of coenzyme. PQQ-GDH has a problem that sugar compounds other than glucose in a sample affect measurements, precluding accurate measurements, because it also reacts with sugar compounds other than glucose to be measured, such as maltose, D-galactose, and D-xylose, because of low substrate specificity.

According to a recent report, during the measurement of the blood glucose level of a patient with diabetes, who received infusion with an SMBG device using PQQ-GDH as a biosensor, PQQ-GDH also reacted with maltose contained in an infusion, raising a measured value as compared with the actual blood glucose level, and the patient developed hypoglycemia due to treatment based on this value. In addition, similar events may occur in patients who participate in a trial on galactose tolerance or xylose absorption (see, for example, Non-patent document 1). In response to this, the Pharmaceutical and Food Safety Bureau, Ministry of Health, Labour and Welfare conducted a cross-reactivity test to investigate the effects of the addition of each sugar into a glucose solution on blood glucose measurements. When maltose was added at 600 mg/dL, D-galactose at 300 mg/dL, and D-xylose at 200 mg/dL, measurements with a blood glucose measurement kit using the PQQ-GDH method were 2.5-3 times higher than the actual glucose level. Specifically, maltose, D-galactose, and D-xylose that may exist in a measurement sample preclude accurate measurement. The development of GDH that allows specific glucose measurement with high substrate specificity without being affected by sugar compounds that cause measurement errors is desired.

Under the above circumstances, GDHs using coenzymes other than those described above have attracted attention. For example, although the substrate specificity has not been described in detail, reports were published regarding a GDH derived from *Aspergillus oryzae* (see, for example, Non-patent documents 2-5). In addition, a glucose dehydrogenase using flavin adenine dinucleotide (FAD) from *Aspergillus* as a coenzyme (FAD-GDH) has been disclosed (see, for example, Patent documents 1-3). An FAD-GDH derived from *Aspergillus*, with reduced effects on D-xylose, has also been disclosed (see, for example, Patent document 4).

As described above, some FAD-GDHs having low reactivity with one or several sugar compounds other than D-glucose are known. However, no flavin-bound GDH having sufficiently low reactivity with all of maltose, D-galactose, and D-xylose is known. In addition, no flavin-bound GDH that allows accurate measurement of glucose levels in the presence of D-glucose, maltose, D-galactose, and D-xylose without being influenced by sugar compounds thereof is known. No flavin-bound GDH having such properties and excellent heat resistance is known, either. In addition, neither method nor means of efficiently producing a flavin-bound GDH having such excellent substrate specificity has been reported.

CITATION LIST

Patent Literature

Patent document 1: Japanese Patent Application Kokai Publication No. 2007-289148
Patent document 2: WO 04/058958
Patent document 3: WO 07/139,013
Patent document 4: Japanese Patent Application Kokai Publication No. 2008-237210

Non-Patent Documents

Non-patent document 1: Pharmaceuticals and Medical Devices Safety Information No. 206, October 2004, Pharmaceutical and Food Safety Bureau, Ministry of Health, Labour and Welfare
Non-patent document 2: Studies on the glucose dehydrogenase of *Aspergillus oryzae*. I. Induction of its synthesis by p-benzoquinone and hydroquinone, T. C. Bak, and R. Sato, Biochim. Biophys. Acta, 139, 265-276 (1967).
Non-patent document 3: Studies on the glucose dehydrogenase of *Aspergillus oryzae*. II. Purification and physical and chemical properties, T. C. Bak, Biochim. Biophys. Acta, 139, 277-293 (1967).
Non-patent document 4: Studies on the glucose dehydrogenase of *Aspergillus oryzae*. III. General enzymatic properties, T. C. Bak, Biochim. Biophys. Acta, 146, 317-327 (1967).
Non-patent document 5: Studies on the glucose dehydrogenase of *Aspergillus oryzae*. IV. Histidyl residue as an active site, T. C. Bak, and R. Sato, Biochim. Biophys. Acta, 146, 328-335 (1967).

DISCLOSURE OF THE INVENTION

Problems to be Solved by the Invention

The purpose of the present invention is to provide heat-resistant flavin-bound glucose dehydrogenases having high substrate specificity for D-glucose, an efficient production method of the same, and a transformant used for the same.

Means for Solving the Problems

To solve the problem described above, the inventors conducted intensive investigations. As a result of screening microorganisms producing novel GDHs that allow accurate measurement of glucose, the inventors found novel GDHs having GDH activity from strains belonging to Mucoromycotina, which are specific for glucose and allows accurate measurement of glucose even in the presence of sugar compounds other than glucose.

The inventors purified these GDH and determined their properties, demonstrating that these enzyme is a novel flavin-bound GDHs. The inventors actually measured D-glucose in the presence of maltose, D-galactose, or D-xylose. The inventors obtained the amino acid sequence of one of the novel GDHs and the gene sequence information encoding the same. In addition, to solve the problem that it is difficult to obtain an enzyme in a sufficient amount from the culture of an original microorganism, intensive investigations were conducted.

As a result, a larger amount of a flavin-bound GDH could be efficiently obtained by introducing a gene encoding the flavin-bound GDH into yeast and culturing the yeast transformant, from the culture. Furthermore, surprisingly, the flavin-bound GDH obtained from the yeast transformant was found to have markedly improved heat resistance as compared with that produced in the original microorganism, thereby completing the invention.

Specifically, the invention relates to:
(1) a flavin-bound glucose dehydrogenase having the following properties (i) to (iv):
(i) action: glucose dehydrogenase activity in the presence of an electron acceptor;
(ii) molecular weight: approximately 80-kDa molecular weight of the polypeptide chain of the protein;
(iii) substrate specificity: lower reactivity to maltose, D-galactose, and D-xylose than that to D-glucose; and
(iv) 50% or above residual activity after heat treatment at 50° C. for 15 minutes;
(2) the flavin-bound glucose dehydrogenase of the above (1), consisting of the amino acid sequence of SEQ ID NO: 1 or 3, an amino acid sequence at least 85% identical to said amino acid sequence, or an amino acid sequence having one or several amino acids deleted, substituted, or added in said amino acid sequence;
(3) the flavin-bound glucose dehydrogenases of the above (1) and (2), characterized by that the flavin-bound GDHs derive from a microorganism classified as Mucoromycotina, preferably Mucoromycetes, more preferably Mucorales, further preferably Mucoraceae and are expressed using yeast as a host;
(4) a yeast transformant obtained by introducing into yeast a gene encoding a flavin-bound glucose dehydrogenase, consisting of the amino acid sequence of SEQ ID NO: 1 or 3, an amino acid sequence at least 85% identical to said amino acid sequence, or an amino acid sequence having one or several amino acids deleted, substituted, or added in said amino acid sequence;
(5) the yeast transformant of the above (4), characterized by that the yeast belongs to *Zygosaccharomyces, Saccharomyces, Pichia*, or *Candida*;
(6) a method for producing a flavin-bound glucose dehydrogenase, characterized by culturing the yeast transformants of the above (4) and (5) and collecting a flavin-bound GDH from said culture; and
(7) a method for producing a flavin-bound glucose dehydrogenase, characterized by culturing a yeast transformant carrying DNA which encodes a protein having flavin-bound GDH enzyme activity and encoding a flavin-bound glucose dehydrogenase gene, consisting of any DNA selected from the group consisting of the following (A) to (E):
(A) DNA encoding the amino acid sequence of SEQ ID NO: 1;
(B) DNA consisting of the base sequence of SEQ ID NO: 2;
(C) DNA encoding the amino acid sequence of SEQ ID NO: 3;
(D) DNA consisting of the base sequence of SEQ ID NO: 4; and
(E) DNA having a base sequence at least 85% identical to the base sequence of SEQ ID NO: 2 or 4, and
collecting a flavin-bound glucose dehydrogenase from said culture.

Effect of the Invention

The yeast transformant of the invention and the method for producing a flavin-bound GDH using the same allow efficient production of a novel flavin-bound GDH having excellent heat resistance, and accurate measurement of D-glucose without being influenced by sugar compounds contained in a measurement sample, such as maltose, D-galactose, and D-xylose. Thus, a practical GDH that allows accurate measurement of blood glucose levels in samples from patients receiving a fluid containing maltose or participating in a trial on galactose load or xylose absorption can be efficiently provided.

BEST MODE FOR CARRYING OUT THE INVENTION

Substrate Specificity of Flavin-Bound GDHs

Figure 1:
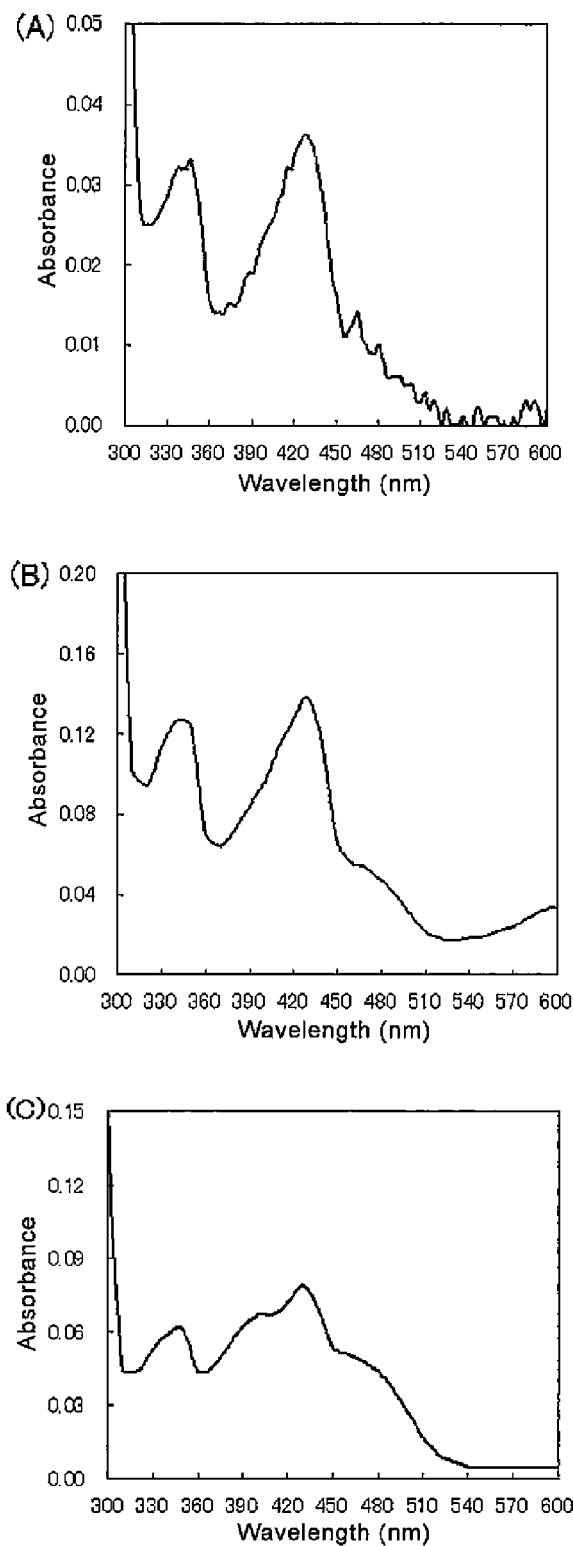
FIG. 1 Absorption spectra of the flavin-bound GDHs used in the invention.

The flavin-bound GDHs used in the invention are characterized by excellent substrate specificity and extremely high selectivity for D-glucose. Specifically, the flavin-bound GDHs used in the invention are poorly reactive to maltose, D-galactose, and D-xylose. Specifically, the flavin-bound GDHs used in the invention are characterized in that the reactivity to maltose, D-galactose, and D-xylose is less than or equal to 2% relative to 100% for reactivity to D-glucose. The flavin-bound GDHs used in the invention have such high substrate specificity. Thus, D-glucose can be accurately measured in samples from patients receiving a infusion containing maltose or undergoing in a galactose tolerance test load or xylose absorption test without being influenced by sugar compounds contained in a measurement sample, such as maltose, D-galactose, and D-xylose.

As described above, the flavin-bound GDHs used in the invention is characterized in that measurements obtained using sugar compounds, such as maltose, D-galactose, and D-xylose, instead of D-glucose, as substrates are very low and that glucose levels can be accurately measured even in the presence of contaminating sugar compounds, such as maltose, D-galactose, and D-xylose. Specifically, measurements obtained in the presence of one or several contaminating sugar compounds selected from maltose, D-galactose, and D-xylose are 96-103% and those obtained in the presence of all the contaminating sugar compounds, maltose, D-galactose, and D-xylose, are 96-104% relative to 100% for reactivity to D-glucose in the absence of these contaminating sugar compounds. Use of the flavin-bound GDHs having such properties preferably allows accurate measurement of glucose levels even in the presence of maltose, D-galactose, and D-xylose in a measurement sample.

(Enzymatic Properties of the Flavin-Bound GDHs Used in the Invention)

Exemplary enzymes preferred as the flavin-bound GDHs used in the invention include those having the following enzymatic properties:
(1) action: GDH activity in the presence of an electron acceptor;
(2) molecular weight: approximately 80-kDa molecular weight of the polypeptide chain of the protein;
(3) substrate specificity: lower reactivity to maltose, D-galactose, and D-xylose than that to D-glucose;
(4) optimum pH: pH 6.5-7.0;
(5) optimum temperature: 37-40° C.;
(6) stable pH range: pH 3.5-7.0
(7) 80% or above residual activity after heat treatment at 40° C. for 15 minutes;
(8) use of flavin compound as a coenzyme; and
(9) Km value: Km value for D-glucose is 26-33 mM.

GDHs having the above enzymatic properties allow accurate measurement of D-glucose without being influenced by sugar compounds contained in a measurement sample, such as maltose, D-galactose, and D-xylose. In addition, the GDHs can be preferably used as measurement reagents for diagnoses, because they act at pH and temperature ranges preferred for applications to clinical diagnoses, such as measurement of blood glucose levels.

Although the above parameters of properties are typical examples, they may vary in an acceptable range that allows achievement of the effects of the invention in measuring D-glucose levels under predetermined measurement conditions. For example, the parameters, such as stable and optimum pH ranges and optimum temperature range, may be slightly wider than the above typical ranges within a range including the predetermined measurement conditions. On the contrary, the parameters may be slightly narrower than the above typical ranges as far as sufficient activity and/or stability are ensured under the measurement conditions. Substrate specificity is generally higher at a smaller Km value. The enzyme of the invention may have a value within a range that substantially realizes satisfactory substrate selection under the predetermined conditions.

The above various enzymatic properties can be examined using known techniques to specify various enzymatic properties, for example, methods described in the Examples below. The various enzymatic properties can be examined to some extent using a culture medium of the flavin-bound GDH-producing microorganism used in the invention or during the intermediate step of a purification process, and can be examined in detail using a purified enzyme.

The purified enzyme is an enzyme isolated substantially free of components other than said enzyme, particularly, free of proteins other than said enzyme (contaminating proteins). Specifically, for example, the content of contaminating proteins on a weight basis is less than about 20%, preferably less than about 10%, more preferably less than about 5%, even more preferably less than about 1% of the total. MpGDH, MjGDH, and McGDH described herein below are purified enzymes, unless otherwise stated.

Electron acceptors utilized by the flavin-bound GDHs used in the invention are, but not particularly limited to, for example, any electron acceptor known as a preferred reagent component used for the measurement of blood glucose levels.

Coenzymes utilized by the flavin-bound GDHs used in the invention are characterized by being flavin compounds. Flavin compounds include, for example, flavin adenine dinucleotide (FAD) and flavin mononucleotide (FMN).

Exemplary enzymes preferred as the flavin-bound GDHs used in the invention include flavin-bound GDHs with approximately 80 kDa of the molecular weight of the polypeptide chain of the protein as measured by SDS-polyacrylamide gel electrophoresis. The flavin-bound GDHs used in the invention may be glycosylated. Thus, without deglycosylation, their molecular weights tend to be larger than their actual values as measured by SDS-polyacrylamide gel electrophoresis.

Exemplary enzymes preferred as the flavin-bound GDHs used in the invention include those with Km values for D-glucose ranging from 26 to 33 mM.

(Action Principle and Activity Assay of the Flavin-Bound GDHs)

The flavin-bound GDHs used in the invention catalyze a reaction for generating glucono-δ-lactone by oxidizing the hydroxyl group of glucose in the presence of an electron acceptor.

Thus, this principle can be employed, for example, to measure the activities of the flavin-bound GDHs used in the invention with the measurement system described below using phenazine methosulfate (PMS) and 2,6-dichloro-indophenol (DCIP) as electron acceptors.

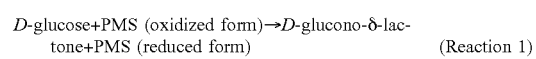
(Reaction 1)

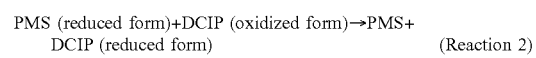
(Reaction 2)

First, in the reaction 1, PMS (reduced form) is generated along with glucose oxidization. In the subsequent reaction 2, DCIP is reduced along with PMS oxidation, allowing measurement of disappeared oxidized DCIP from the amount of change in absorbance at 600-nm wavelength.

Specifically, the activities of the flavin-bound GDHs are measured according to the following procedures. To initiate a reaction, 1.79 mL of 100 mM phosphate buffer (pH7.0), 0.08 mL of 1.25 M D-glucose solution, and 0.01 mL of 20 mM DCIP solution are mixed, followed by incubation at 37° C. for 5 minutes, and, subsequently, 0.02 mL of 20 mM PMS solution and 0.1 mL of an enzyme sample solution are added. Absorbance is measured at the initiation of the reaction and over time to determine a decrease in the absorbance at 600 nm ($\Delta A600$) per minute due to the progress of the enzyme reaction and calculate flavin-bound GDH activity according to the following formula. At that time, one unit of the flavin-bound GDH activity is defined as the amount of an enzyme that reduces 1 μmol of DCIP at 37° C. in one minute in the presence of 50 mM D-glucose.

$$GDH\ \text{activity}(U/\text{ml}) = \frac{-(\Delta A600 - \Delta A600_{blank}) \times 2.0 \times df}{16.3 \times 0.1 \times 1.0} \quad \text{[Formula 1]}$$

The formula indicates 2.0 as the liquid volume (mL) of reaction reagent plus enzyme reagent, 16.3 as millimolar extinction coefficient (cm$^2$/μmol) under the activity assay conditions, 0.1 as the liquid volume (mL) of an enzyme solution, 1.0 as the optical path length (cm) of a cell, $\Delta A600_{blank}$ as a decrease in the absorbance at 600 nm per minute when 10 mM acetate buffer, instead of an enzyme sample solution, is added to initiate a reaction, and df as a dilution factor.

(Derivations of the Flavin-Bound GDHs)

The flavin-bound GDHs having the above properties, used in the invention, can be obtained from a microorganism classified as Mucoromycotina, preferably Mucoromycetes, more preferably Mucorales, further preferably Mucoraceae. Microorganisms classified as Mucoromycotina, preferably Mucoromycetes, more preferably Mucorales, further preferably Mucoraceae include, for example, *Mucor, Absidia*, and *Actinomucor*. Specific examples of preferred microorganisms which are classified as *Mucor* and produce the flavin-bound GDHs used in the invention include *Mucor prainii, Mucor javanicus*, and *Mucor circinelloides* f. *circinelloides*. Specifically, they include *Mucor prainii* NISL0103, *Mucor javanicus* NISL0111, and *Mucor circinelloides* f. *circinelloides* NISL0117. Specific examples of preferred microorganisms which are classified as *Absidia* and produce the flavin-bound GDHs used in the invention include *Absidia cylindrospora* and *Absidia hyalospora*. Specifically, they include *Absidia cylindrospora* NISL0211 and *Absidia hyalospora* NISL0218. Specific examples of preferred microorganisms which are classified as *Actinomucor* and produce the flavin-bound GDHs used in the invention include *Actinomucor elegans*. Specifically, they include *Actinomucor elegans* NISL9082. The above strains are stored at the Noda Institute for Scientific Research (NISL) and are available through prescribed procedures.

As described above, the flavin-bound GDHs used in the invention are those that derive from a microorganism classified as Mucoromycotina, preferably Mucoromycetes, more preferably Mucorales, further preferably Mucoraceae and have the various properties described above. Furthermore, a recombinant flavin-bound GDH produced by using a gene encoding a flavin-bound GDH, obtained by a known genetic engineering technique from the flavin-bound GDH-producing microorganisms, partially modifying it as needed, and introducing it into a suitable host microorganism by known various techniques is also included in the flavin-bound GDHs that derive from a microorganism classified as Mucoromycotina, preferably Mucoromycetes, more preferably Mucorales, further preferably Mucoraceae and have the various properties described above, used in the invention. Similarly, regarding flavin-bound GDHs that derive from a microorganism classified as *Mucor* or are described with the strain name of a specific producer microorganism, flavin-bound GDHs that are obtained based on genetic information from each microorganism and have the various properties described above are also included in the invention.

(Amino Acid Sequences of Flavin-Bound GDHs)

The flavin-bound GDHs used in the invention are characterized by having the amino acid sequence of SEQ ID NO: 1 or 3, an amino acid sequence at least 85% identical to said amino acid sequence, or an amino acid sequence having one or several amino acids deleted, substituted, or added in said amino acid sequence. The flavin-bound GDH having the amino acid sequence of SEQ ID NO: 1 or 3 have the above various properties. In addition, GDHs having an amino acid sequence at least 85%, preferably 90%, most preferably 95% or above identical to the amino acid sequence of SEQ ID NO: 1 or 3 and having the same various properties as the flavin-bound GDH having the amino acid sequence of SEQ ID NO: 1 or 3 are also included in the flavin-bound GDHs of the invention.

(Gene Sequences Encoding Flavin-Bound GDHs)

The genes encoding the flavin-bound GDHs used in the invention refer to DNAs encoding flavin-bound GDHs having the amino acid sequence of SEQ ID NO: 1 or 3, an amino acid sequence at least 85% identical to said amino acid sequence, or an amino acid sequence having one or several amino acids deleted, substituted, or added in said amino acid sequence. The genes encoding the flavin-bound GDHs used in the invention refer to DNAs consisting of a base sequence of SEQ ID NO: 2 or 4. Alternatively, the genes encoding the flavin-bound GDHs used in the invention refer to DNAs having an base sequence at least 85%, preferably 90%, most preferably 95% or above identical to the base sequence of SEQ ID NO: 2 or 4 and encoding proteins having flavin-bound GDH enzyme activity.

(Vectors Containing Gene Sequences Encoding Flavin-Bound GDHs and Transformants)

The genes encoding the flavin-bound GDHs used in the invention may be inserted into known various suitable vectors. Furthermore, these vectors may be introduced into known various suitable hosts to generate transformants introduced with recombinant DNAs containing flavin-bound GDH genes. Methods for obtaining these genes, gene sequence information, and amino acid sequence information and generating various vectors and transformants are known to those skilled in the art. Some examples are described below.

A routine gene cloning methods are employed to obtain a flavin-bound GDH gene from a flavin-bound GDH-producing microorganism. For example, chromosomal DNA or mRNA can be extracted from microorganisms and cells with a flavin-bound GDH-producing ability using routine methods, such as those described in Current Protocols in Molecular Biology (WILEY Interscience, 1989). Furthermore, cDNA can be synthesized using in RNA as a template. The above chromosomal DNA or cDNA can be used to generate a chromosomal DNA or cDNA library.

Subsequently, an appropriate DNA probe is synthesized based on the amino acid sequence of a flavin-bound GDH. This probe is used to screen a chromosomal DNA or cDNA library. Alternatively, appropriate DNA primers are generated based on the above amino acid sequences to amplify DNA fragments containing gene fragments of interest using polymerase chain reaction (PCR), such as 5' or 3' RACE method. The DNA fragments, thus obtained, can be ligated to obtain a DNA fragment containing a full-length gene of interest.

Preferred examples of the genes encoding flavin-bound GDHs, thus obtained, include a flavin-bound GDH gene derived from *Mucor*. These genes are preferably ligated to various vectors using routine methods to facilitate handling. For example, a recombinant plasmid containing an isolated gene encoding a flavin-bound GDH derived from *Mucor* is generated. The gene can be extracted and purified from the plasmid using, for example, QIAGEN (QIAGEN). DNA vectors that can be used in the invention include, for example, DNA plasmid and bacteriophage vectors. Specifically, for example, pBluescriptII SK+ (STRATAGENE) is preferred.

The base sequence of the flavin-bound GDH gene, obtained by the above method, may be determined and confirmed using, for example, multi-capillary DNA analysis system CEQ2000 (Beckman Coulter, Inc.).

The resulting flavin-bound GDH gene can be transformed or introduced by a routine method. Specifically, for example, the flavin-bound GDH gene can be inserted directly into host chromosome using homologous recombination or transposon or ligated to plasmid, cosmid, phage, virus, or artificial chromosome vector to be introduced into a host.

The above inserted gene may contain a marker gene that allows selection of transformed cells. Marker genes include, for example, genes that complement host auxotrophy, such as URA3 and TRP1. Inserted genes desirably contain a promoter that facilitates the expression of the gene of the invention in host cells or other regulatory sequences (e.g., enhancer, terminator, and polyadenylation sequences). Specifically, promoters include, for example, GAL1 and ADH1 promoters.

(Hosts Used for the Transformant of the Invention)

Exemplary hosts used for the transformant of the invention include yeast. Microorganisms classified as yeast include, for example, yeasts belonging to *Zygosaccharomyces, Saccharomyces, Pichia*, or *Candida*. Specifically, preferred microorganisms that are classified in these genera and used in the invention to produce the flavin-bound GDHs include *Zygosaccharomyces rouxii, Saccharomyces cerevisiae, Saccharomyces pombe, Pichia pastoris*, and *Candida antarctica*. More specifically, they include *Zygosaccharomyces rouxii* IFO1876.

(Transformation of Yeast)

The invention uses yeast as a host. Preferred methods for transforming yeast include, but are not limited to, known methods, such as a method with lithium acetate (Methods Mol. Cell. Biol., 5, 255-269 (1995)) and electroporation (J Microbial Methods 55 (2003) 481-484). Transformation may be performed using various techniques, including spheroplast and glass bead methods.

(Production of a Flavin-Bound GDH)

The transformant obtained by the above transformation is used to produce a flavin-bound GDH. Specifically, the yeast transformant obtained by the above transformation is cultured to obtain a flavin-bound glucose dehydrogenase from the culture.

A technique for producing a certain useful protein by introducing a gene encoding the protein into a heterologous host is theoretically known. However, in fact, its effectiveness varies with the kinds of genes and heterologous hosts used for introduction. Often, a gene cannot be introduced into or expressed in a heterologous host. Specifically, it is difficult to find a combination of gene, host, and introduction method to facilitate the production of substances. Thus, it is industrially useful to find a combination of gene, host, and introduction method to achieve efficient production.

Significantly more efficient enzyme production can be achieved by culturing the yeast transformant of the invention than by culturing the microorganism (i.e., *Mucor*) from which the flavin-bound GDH used in the invention derives. Specifically, the amounts of enzyme expression increase inside or outside of the cultured cell. Furthermore, the secretory pattern of an enzyme expressed varies with hosts, allowing efficient production. For example, a flavin-bound GDH produced through the culture of a yeast transformant obtained by transforming yeast, *Zygosaccharomyces*, with a gene expression cassette containing a flavin-bound GDH gene derived from *Mucor* is mostly excreted outside of the cell. Thus, it is a preferred effect of the invention to facilitate enzyme purification through secretory production of an enzyme of interest outside of the bacteria.

For example, the various flavin-bound GDHs derived from *Mucor*, used in the invention, are not produced in a sufficient amount when cultured in the original microorganism, requiring a larger scale of cultivation and an additional process to extract an enzyme from the cultured cell.

(Culture of Yeast Transformant)

The yeast transformant of the invention is preferably cultured in an YPD liquid medium (2% Bacto-peptone, 1% Bacto-yeast extract, and 2% glucose) widely used for the culture of *Saccharomyces cerevisiae*. In addition, nutrient sources or components, which can increase the production of the flavin-bound GDH used in the invention when added, may be used alone or in combination.

Assimilable carbon compounds (e.g., glucose, starch hydrolyzate, glycerin, fructose, and syrup) may be used as carbon sources. Available nitrogen compounds (e.g., yeast extract, peptone, meat extract, corn steep liquor, soy flour, malt extract, amino acids, ammonium sulfate, and ammonium nitrate) may be used as nitrogen sources. Inorganic substances include, for example, various salts, such as sodium chloride, potassium chloride, magnesium sulfate, manganese chloride, ferrous sulfate, monopotassium phosphate, dipotassium phosphate, sodium carbonate, and calcium chloride. In addition, vitamins and antifoaming agents may be added as needed.

Culture conditions may vary with microorganisms to be cultured. For example, the initial pH of medium may be adjusted to 5-10, culture temperature to 20-40° C., culture time to 15-25 hours, 1-2 days, or 10-50 hours as needed. Any culture methods, such as aeration-agitation submerged culture, shaking culture, and static culture, may be employed. One example of medium and culture conditions to culture yeast, *Zygosaccharomyces*, is shaking at 200 rpm at 30° C. for 24 hours in a medium (2% Bacto-peptone, 1% Bacto-yeast extract, and 2% glucose). An additional example of medium and culture conditions to culture the original *Mucor* strain, an original microorganism that produces the GDH used in the invention, is shaking at 130 rpm at 30° C. for 2-5 or 3-5 days in a medium (2.0% Yeast extract, 4% glucose, pH 6.0). Optimizing culture conditions depending on the transformants to be used in the invention shortens culture time and increases enzyme production, contributing to efficient enzyme production.

After the completion of the culture, routine procedures for enzyme collection may be employed to collect a flavin-bound GDH from the culture or the cultured cell. If the enzyme exists intracellularly, the cells are preferably separated by procedures, such as filtration and centrifugation, to extract the intracellular enzyme. For example, methods for crushing bacteria using routine procedures, such as sonicator, French press, and Dyno-Mill, and methods for lysing cell wall using cell wall lytic enzymes, such as lysozyme, and methods for extracting intracellular enzyme from bacteria using surfactants, such as Triton X-100, can be employed alone or in combination. If the enzyme exists outside of cells, the cells are preferably separated by procedures, such as filtration and centrifugation, to collect a supernatant.

Subsequently, insolubles are removed by filtration or centrifugation to obtain an enzyme extract. To isolate and purify a flavin-bound GDH from the obtained extract as needed, nucleic acid is removed as needed, and ammonium sulfate, alcohol, and acetone are added, followed by fractionation to obtain a precipitate. To obtain an enzyme preparation of higher purity, gel filtration using Sephadex, Ultra gel, or Bio-Gel, adsorption elution using ion exchanger or hydroxyapatite, affinity chromatography, fractionation using a molecular sieve or hollow fiber membrane, for example, are appropriately selected or combined.

The flavin-bound GDH used in the invention may be modified in its gene or amino acid sequence through partial deletion, substitution, addition, and/or insertion using known gene engineering techniques. Such flavin-bound GDHs to which desired properties are conferred can also be efficiently produced using the yeast transformant of the invention.

The flavin-bound GDHs produced as described above allow accurate measurement of glucose levels even in the presence of contaminating sugar compounds and, therefore, can be preferably applied to glucose sensors.

Hereinafter, the invention is more specifically described with Examples. However, they are not intended to limit the scope of the invention.

Example 1

Acquisition of a Flavin-Bound GDH Derived from *Mucor*

1. Screening of GDH-Producing Cells

Strains isolated from natural environments and about 500 stored strains supplied by a culture collection institution (Noda Institute for Scientific Research) were screened for GDH production. Each bacterial strain under test was inoculated into 3 mL of malt extract medium (2.0% malt extract, 2.0% D-glucose, 0.1% polypeptone, pH 6.0), followed by shaking culture at 30° C. for 3-5 days. The culture medium was centrifuged at 800×g for 10 minutes to precipitate cells. Subsequently, the cells were suspended in 10 mM acetate buffer (pH 5.0) and homogenized using a Multi-beads Shocker (Yasui Kikai) (2,000 rpm, 60 seconds, 16 times). The supernatant collected by centrifugation at 20,000×g and 4° C. for 10 minutes was used as a crude enzyme solution.

2. Determination of GDH Activity

Solutions were mixed according to the following procedures, followed by absorbance measurement to examine GDH activity in the crude enzyme solution. To initiate a reaction, 1.79 mL of 100 mM phosphate buffer (pH 7.0), 0.08 mL of 1.25 M D-glucose solution, and 0.01 mL of 20 mM DCIP solution were mixed, followed by incubation at 37° C. for five minutes, and 0.02 mL of 20 mM PMS solution and 0.1 mL of an enzyme sample solution were added. A decrease in the absorbance at 600 nm ($\Delta A600$) per minute due to the progress of the enzyme reaction after the initiation of the reaction was determined to calculate GDH activity according to the following formula. At that time, one unit of GDH activity is defined as the amount of an enzyme that reduces 1 µmol of DCIP at 37° C. within one minute in the presence of 50 mM D-glucose.

$$GDH\ \text{activity}(U/\text{ml}) = \frac{-(\Delta A600 - \Delta A600_{blank}) \times 2.0 \times df}{16.3 \times 0.1 \times 1.0} \quad \text{[Formula 2]}$$

The formula indicates 2.0 as the liquid volume (mL) of reaction reagent plus enzyme reagent, 16.3 as millimolar extinction coefficient (cm$^2$/µmol) under the activity assay conditions, 0.1 as the liquid volume (mL) of an enzyme solution, 1.0 as the optical path length (cm) of a cell, $\Delta A600_{blank}$ as a decrease in the absorbance at 600 nm per minute when 10 mM acetate buffer, instead of an enzyme sample solution, is added to initiate a reaction, and df as a dilution factor.

The presence or absence of GDH activity was investigated in the crude enzyme solutions from each strain according to the above activity assay. Table 1 shows the results.

TABLE 1

| GDH activity detected in the crude enzyme solution | |
|---|---|
| Strain | Activity (U/mL) |
| *Mucor prainii* NISL0103 | 0.187 |
| *Mucor javanicus* NISL0107 | 0.476 |
| *Mucor javanicus* NISL0108 | 0.023 |
| *Mucor javanicus* NISL0111 | 0.714 |
| *Mucor javanicus* NISL0112 | 0.282 |
| *Mucor javanicus* NISL0115 | 0.116 |
| *Mucor circinelloides* f. *circinelloides* NISL0116 | 0.033 |
| *Mucor circinelloides* f. *circinelloides* NISL0117 | 0.136 |
| *Mucor hiemalis* f. *silvaticus* NISL0118 | 0.001 |
| *Absidia cylindrospora* NISL0211 | 0.007 |
| *Absidia hyalospora* NISL0218 | 0.006 |
| *Actinomucor elegans* NISL9082 | 0.012 |

As a result, GDH activity was detected in the crude enzyme solutions derived from *Mucor prainii* NISL0103, *Mucor javanicus* NISL0107, *Mucor javanicus* NISL0108, *Mucor javanicus* NISL0111, *Mucor javanicus* NISL0112, *Mucor javanicus* NISL0115, *Mucor circinelloides* f. *circinelloides* NISL0116, *Mucor circinelloides* f. *circinelloides* NISL0117, *Mucor hiemalis* f. *silvaticus* NISL0118, *Absidia cylindrospora* NISL0211, *Absidia hyalospora* NISL0218, and *Actinomucor elegans* NISL9082.

Example 2

Purification of a Flavin-Bound GDH Derived from *Mucor*

To a 0.5 L Sakaguchi flask, 0.1 L of preculture medium (2.0% yeast extract, 4% glucose, pH 6.0) was added. Into the flask, about 1 cm$^2$ each of a preculture of *Mucor prainii*

NISL0103, *Mucor javanicus* NISL0111, or *Mucor circinelloides* f. *circinelloides* NISL0117 on a plate was inoculated, followed by shaking culture at 130 rpm and 30° C. for two days. This was used as a seed culture. Into 20 L of the above medium in a 30 L jar fermenter (two jar fermenters), 0.2 L each of the seed culture was inoculated, followed by culture at 200 rpm, 30° C., and 0.5 vvm for three days. After the completion of the culture, 40 L of culture medium was filtered through a filter cloth to collect cells. Subsequently, the obtained cells were suspended in 10 mM acetate buffer (pH 5.0).

The above cells suspension was sent to a Dyno-Mill (150 mL/min) and homogenized. The supernatant was collected by centrifugation at 6,000×g for 30 minutes. This supernatant was concentrated using a hollow fiber membrane AIP2013 (Asahi Kasei Chemicals) with 6,000 molecular weight cut off. The concentrated enzyme solution was gradually added to achieve 70% saturation of ammonium sulfate to precipitate excess proteins. This was allowed to stand overnight at 4° C., followed by centrifugation (20,000×g, 60 minutes) to collect a supernatant.

The supernatant was subjected to a Toyopearl Butyl-650 (Tosoh) column (26ϕ×28.5 cm), pre-equilibrated with buffer A (10 mM acetate buffer, 2 M ammonium sulfate, pH 5.0), for elution by linear gradient from buffer A to B (10 mM acetate buffer, pH 5.0). The eluted active fraction was concentrated using a Centricon Plus-70 (Millipore), dialyzed using buffer C (10 mM acetate buffer, pH 4.5), and was subjected to an SP Sepharose FastFlow (GE Healthcare) column (26ϕ×28.5 cm), pre-equilibrated with buffer C, for elution by linear gradient from buffer C to D (10 mM acetate buffer, 200 mM potassium chloride, pH 4.5). The eluted active fraction was concentrated to obtain purified enzyme.

Hereinafter, regarding the purified enzymes, GDHs derived from *Mucor prainii* NISL0103, *Mucor javanicus* NISL0111, and *Mucor circinelloides* f. *circinelloides* NISL0117 are referred to as MpGDH, MjGDH, and McGDH, respectively.

Example 3

Investigation of the Enzymatic Properties of Flavin-Bound GDH Derived from *Mucor*

The properties of the purified GDHs obtained in Example 2 were investigated.
(a) Measurement of Absorption Spectra MpGDH, MjGDH, and McGDH were dialyzed using 10 mM acetate buffer (pH 5.0), followed by the measurement of absorption spectra at 250-800 nm using a spectrophotometer U-3010 (Hitachi High-Technologies Co., Ltd.). FIG. 1 shows the measurement results (FIGS. 1 (A), (B), and (C) show the absorption spectra of MpGDH, MjGDH, and McGDH, respectively.). All the GDHs showed two maximal peaks at around 340-350 and 420-430 nm wavelengths, strongly suggesting that the GDHs of the invention are flavin-bound proteins because these absorption spectra are specific to a flavin enzyme.
(b) Measurement of GOD Activity MpGDH, MjGDH, and McGDH obtained in Example 2 and a commercial glucose oxidase derived from *Aspergillus niger* (GOD, biozyme laboratories) were used to measure GDH and GOD activities. Table 2 shows the results.

GDH activity was measured as described in Example 1. GOD activity was measured using 4-aminoantipyrine (4-AA) and N-ethyl-N-(2-hydroxy-3-sulfopropyl)-3-methylaniline (TOOS) as described below. To initiate a reaction, 30.0 mL of 100 mM phosphate buffer (pH 7.0), 6.0 mL of 833 mM D-glucose solution, 0.3 mL of 25 mM 4-AA solution, 0.3 mL of 40 mM TOOS solution, and 0.3 mL of 500 U/mL POD solution were mixed, of which 3.0 mL was transferred into a test tube and incubated at 37° C. for five minutes, and 0.1 mL of an enzyme sample solution was added. An increase in the absorbance at 555 nm (ΔA555) per minute due to the progress of the enzyme reaction was determined to calculate GOD activity according to the following formula. At that time, one unit of the GOD activity is defined as the amount of an enzyme that generates 1 μmol of $H_2O_2$ at 37° C. within one minute in the presence of 131 mM D-glucose.

$$GOD\ \text{activity}(U/\text{ml}) = \frac{-(\Delta A555 - \Delta A555_{blank}) \times 3.1 \times df}{32.8 \times 0.5 \times 0.1 \times 1.0} \quad \text{[Formula 3]}$$

The formula indicates 3.1 as the liquid volume (mL) of reaction reagent plus enzyme reagent, 32.8 as millimolar extinction coefficient ($cm^2/\mu mol$) under the activity assay conditions, 0.5 as the number of quinoneimine dye molecules generated when one $H_2O_2$ molecule is reduced, 0.1 as the liquid volume (mL) of an enzyme solution, 1.0 as the optical path length (cm) of a cell, $\Delta A555_{blank}$ as an increase in the absorbance at 555 nm per minute when 10 mM acetate buffer, instead of an enzyme sample solution, is added to initiate a reaction, and df as a dilution factor.

TABLE 2

Comparison between the GDH and GOD activities of each enzyme

|  | GDH activity | GOD activity |
| --- | --- | --- |
| MpGDH | 8.80 U/mL | 0.00 U/mL |
| MjGDH | 9.90 U/mL | 0.00 U/mL |
| McGDH | 9.42 U/mL | 0.00 U/mL |
| GOD derived from *Aspergillus niger* | 3.50 U/mL | 9.38 U/mL |

Figure 2:
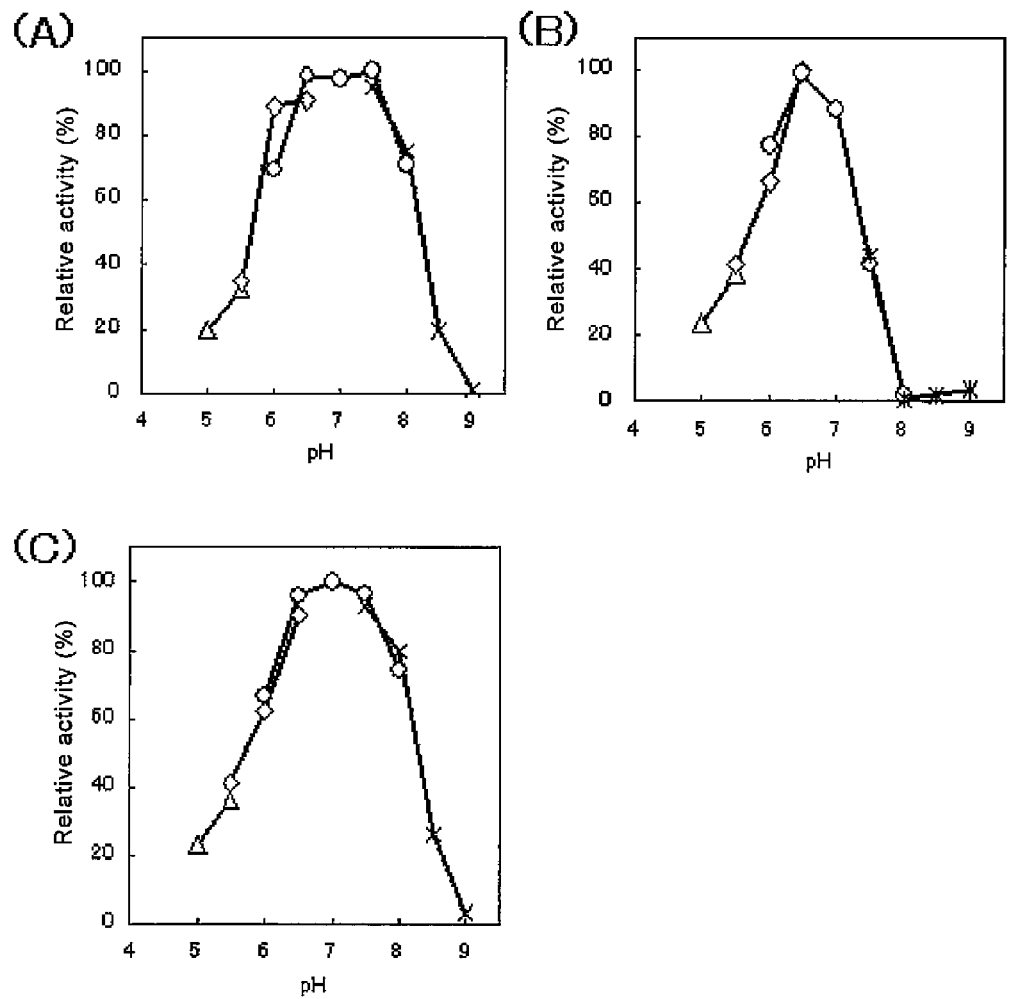
FIG. 2 Optimum pH of the flavin-bound GDHs used in the invention.

As shown in Table 2, MpGDH, MjGDH, and McGDH showed no GOD activity and showed exclusively GDH activity. On the other hand, GOD was demonstrated to show mainly GOD activity and simultaneously have GDH activity. Specifically, the GDH of the invention utilizes no oxygen as an electron acceptor and, therefore, is unlikely to be influenced by the dissolved oxygen of the reaction system in the measurement of D-glucose.
(c) Optimum pH The optimum pH of the above flavin-bound GDH was investigated. FIG. 2 shows the results (FIGS. 2 (A), (B), and (C) show the results of MpGDH, MjGDH, and McGDH, respectively.). Specifically, 100 mM potassium acetate buffer (pH 5.0-5.5, plotted with triangle mark), 100 mM MES-NaOH buffer (pH 5.5-6.5, plotted with diamond mark), 100 mM potassium phosphate buffer (pH 6.0-8.0, plotted with circle mark), and 100 mM Tris-HCl buffer (pH 7.5-9.0, plotted with cross mark) were used to carry out enzyme reactions at 37° C. at each pH in order to compare relative activities.

As a result, all the above flavin-bound GDHs showed the highest activity at pH 6.5 or 7.0 and had optimum pH at around 7.0. Individually, MpGDH and McGDH showed the highest relative activity at pH 7.0 and 80% or above of the maximum relative activity at pH 6.5-7.5, allowing preferable use in this range. MjGDH showed the highest relative activity at pH 6.5 and 80% or above of the maximum relative activity at pH 6.0-7.0, allowing preferable use in this range.

(d) Optimum Temperature Range

Figure 3:
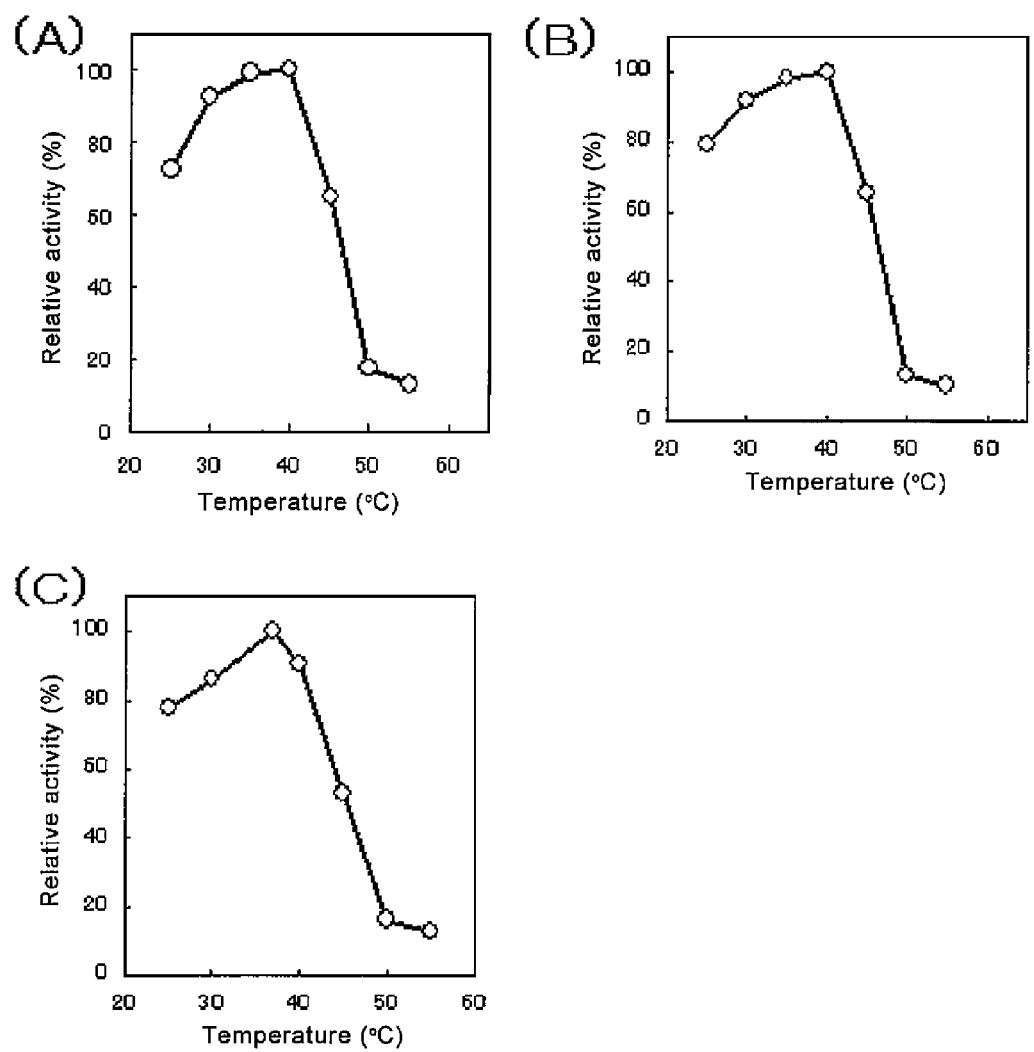
FIG. 3 Optimum temperature of the flavin-bound GDHs used in the invention.

The activity of the enzyme was measured at various temperatures according to the activity assay described in Example 1. Specifically, to initiate a reaction at each temperature, 1.79 mL of 100 mM phosphate buffer (pH 7.0), 0.08 mL of 1.25 M D-glucose solution, and 0.01 mL of 20 mM DCIP solution were mixed, followed by incubation at each temperature, instead of 37° C., for five minutes, and 0.02 mL of 20 mM PMS solution and 0.1 mL of an enzyme sample solution were added. Absorbance was measured at the initiation of the reaction and two minutes later to determine a decrease in the absorbance at 600 nm per minute due to the progress of the enzyme reaction. FIG. 3 shows the results (FIGS. 3 (A), (B), and (C) show the results of MpGDH, MjGDH, and McGDH, respectively.). All of them showed the maximum activity at around 37° C. The temperature range that showed 80% or above activity relative to the maximum one was 30-40° C. Thus, the optimum temperature range of the flavin-bound GDH of the invention was 30-40° C. The most preferable temperature was 37° C.

(e) Km Values for D-Glucose

In the above activity assay, activity was measured by changing the concentration of D-glucose as a substrate to determine the Michaelis constant (Km) from a Lineweaver-Burk plot. As a result, the Km values for D-glucose were 31.1 mM for MpGDH, 26.4 mM for MjGDH, and 33.2 mM for McGDH.

(f) Thermal Stability

Figure 4:
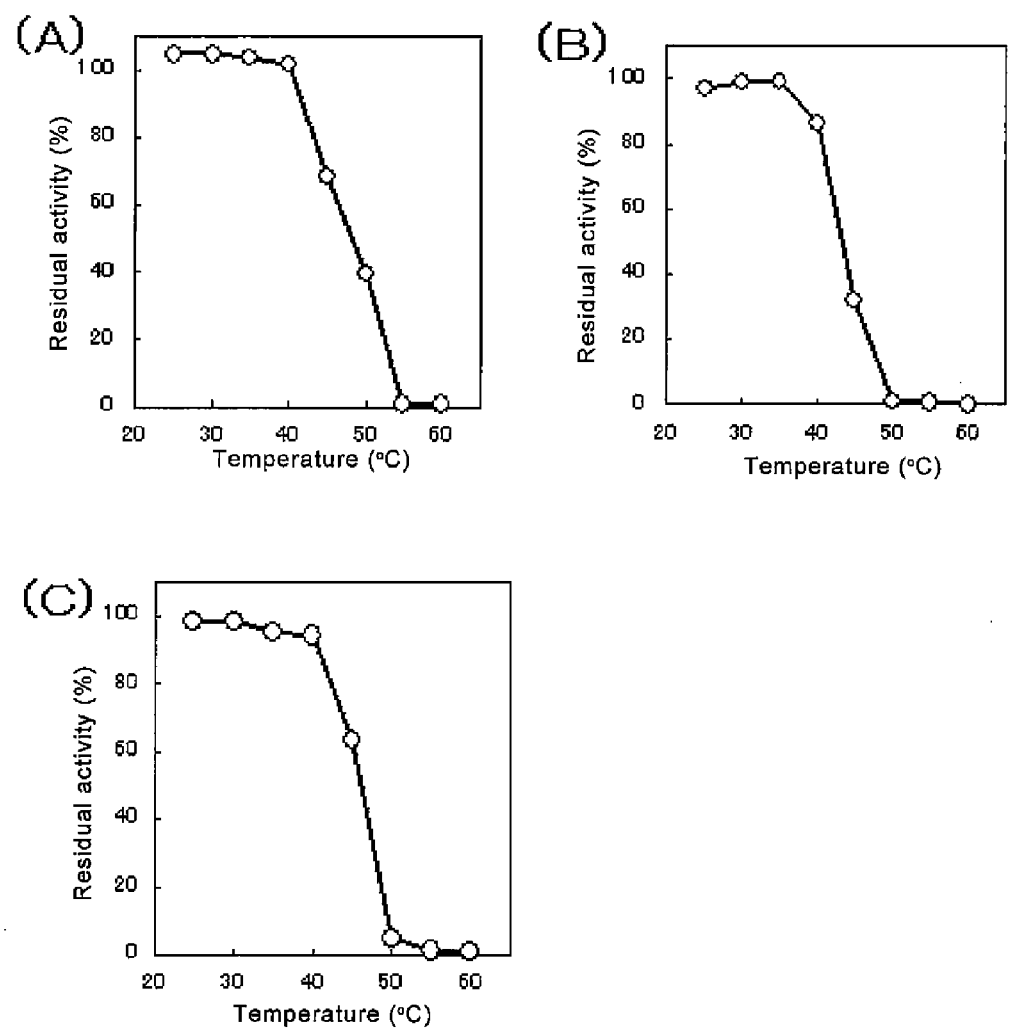
FIG. 4 Thermal stability of the flavin-bound GDHs used in the invention.

FIG. 4 shows the results of the thermal stability of the flavin-bound GDHs of the invention, treated with 100 mM potassium acetate buffer (pH 5.0) at each temperature for 15 minutes (FIGS. 4 (A), (B), and (C) show the results of MpGDH, MjGDH, and McGDH, respectively.). The flavin-bound GDHs of the invention had 80% or above residual activity after heat treatment at 40° C. for 15 minutes, demonstrating that they were stable up to about 40° C.

(g) Range of Stable pH

Figure 5:
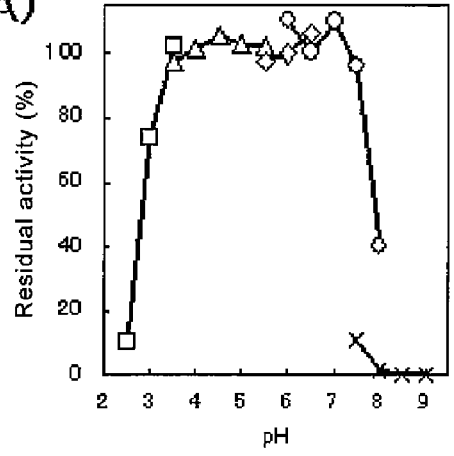
FIG. 5 pH stability of the flavin-bound GDHs used in the invention.
Figure 5:
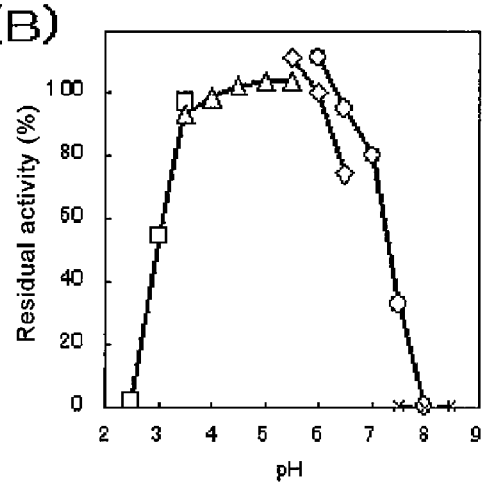
Figure 5:
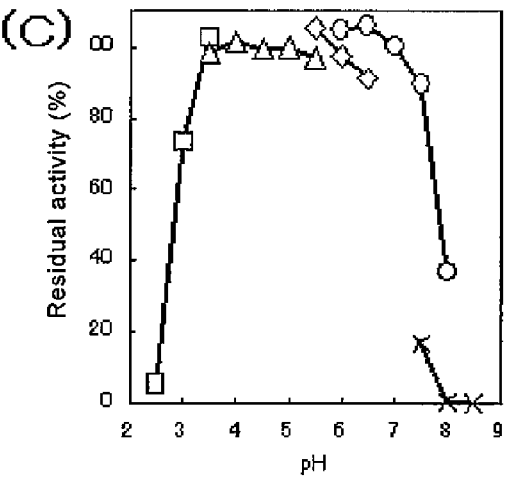

Subsequently, the stable pH of these flavin-bound GDHs was examined. FIG. 5 shows the results (FIGS. 5 (A), (B), and (C) show the results of MpGDH, MjGDH, and McGDH, respectively.). Specifically, 100 mM glycine-HCl buffer (pH 2.5-3.5, plotted with square mark), 100 mM potassium acetate buffer (pH 3.5-5.5, plotted with triangle mark), 100 mM MES-NaOH buffer (pH 5.5-6.5, plotted with diamond mark), 100 mM potassium phosphate buffer (pH 6.0-8.0, plotted with circle mark), and 100 mM Tris-HCl buffer (pH 7.5-9.0, plotted with cross mark) were used to carry out treatment at each pH and at 25° C. for 16 hours, followed by measurement of the residual activity of the flavin-bound GDH. As a result, the pH range that showed 80% or above activity relative to the activity at around pH 5.0 that showed maximum residual activity was pH 3.5-7.0. Thus, the stable pH range of these flavin-bound GDHs was demonstrated to be pH 3.5-7.0.

(h) Molecular Weight

Figure 6:
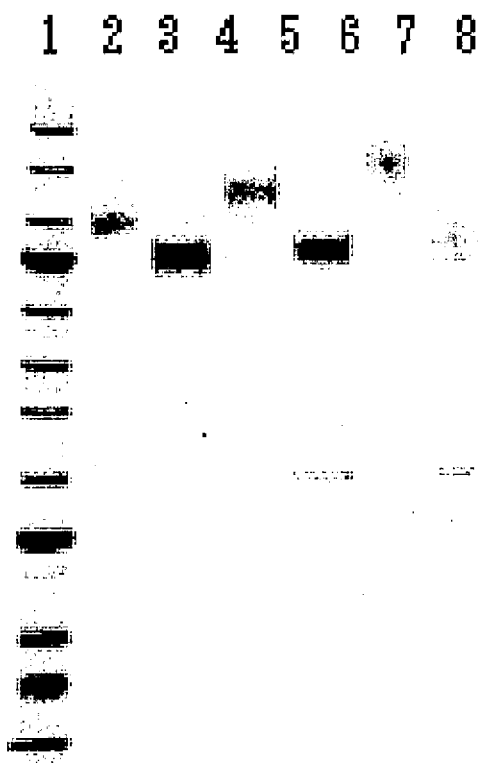
FIG. 6 SDS-polyacrylamide gel electrophoresis of the flavin-bound GDHs used in the invention.

The molecular weights of MpGDH, MjGDH, and McGDH were determined by SDS-polyacrylamide electrophoresis with SuperSep Ace 10-20% (Wako Pure Chemical Industries, Ltd.). Each flavin-bound GDH was deglycosylated using a deglycosylation kit (Enzymatic Deglycosylation Kit, PZM) and electrophoresed in the same manner. FIG. 6 shows the results. The electrophoresed samples are as follows:
Lane 1: Molecular weight markers (New England Biolabs, Inc., protein ladder (10-250 kDa), 250 kDa, 150 kDa, 100 kDa, 80 kDa, 60 kDa, 50 kDa, 40 kDa, 30 kDa, 25 kDa, 20 kDa, and 15 kDa from the top)
Lane 2: MpGDH
Lane 3: Deglycosylated MpGDH
Lane 4: MjGDH
Lane 5: Deglycosylated MjGDH
Lane 6: McGDH
Lane 7: Deglycosylated McGDH
Lane 8: Enzyme used for deglycosylation As shown in FIG. 6, the molecular weights of these flavin-bound GDHs are about 90-130 kDa for MpGDH, about 100-150 kDa for MjGDH, and about 130-200 kDa for McGDH. The molecular weight after deglycosylation using a deglycosylation kit (Enzymatic Deglycosylation Kit, PZM) was about 80 kDa for all of MpGDH, MjGDH, and McGDH.

(i) Substrate Specificity

According to the enzyme activity assay of Example 1, D-glucose, maltose, D-galactose, D-xylose, mannose, sucrose, trehalose, maltotriose, and maltotetraose were used as substrates to measure the activities of the flavin-bound GDHs for each substrate. Substrate specificity was determined to be 50 mM. Table 3 shows the results.

TABLE 3

Relative activities for the substrates of each GDH

| | Relative activity (%) | | | | |
|---|---|---|---|---|---|
| Substrate | MpGDH | MjGDH | McGDH | Patent document 2 GDH | Patent document 3 GDH |
| D-Glucose | 100 | 100 | 100 | 100 | 100 |
| Maltose | 1.09 | 0.72 | 1.25 | 1.4 | 0.00 |
| D-Galactose | 0.44 | 0.54 | 1.25 | 1.2 | — |
| D-Xylose | 1.53 | 1.43 | 2.00 | 9.1 | 17.6 |
| Mannose | 0.66 | 0.36 | 1.00 | 2.8 | 1.40 |
| Sucrose | 0.00 | 0.36 | 0.25 | 0.1> | — |
| Trehalose | 0.22 | 0.00 | 0.25 | 1.7 | — |
| Maltotriose | 0.88 | 0.54 | 1.00 | — | — |
| Maltotetraose | 0.66 | 0.54 | 1.50 | — | — |

As a result, these flavin-bound GDHs were demonstrated to have very low reactivity to each sugar compound, relative to 100% of the activity to D-glucose. Activities to maltose, D-galactose, D-xylose were all 2% or below.

(j) Inhibitory Effects of 1,10-phenanthroline

The inhibitory effects of 1,10-phenanthroline on the activities of these flavin-bound GDHs were examined by the following method. According to the enzyme activity assay of Example 1, the enzyme activities when 1,10-phenanthroline was added at final concentrations of 1, 5, 10, 25, and 50 mM were determined to calculate the inhibitory rates relative to 0% of the inhibitory rate when no 1,10-phenanthroline was added. Table 4 shows the results.

TABLE 4

Inhibitory effects of 1,10-phenanthroline

| Final concentration of | GDH inhibition rate (%) | | |
|---|---|---|---|
| 1,10-phenanthroline (mM) | MpGDH | MjGDH | McGDH |
| 0 | 0 | 0 | 0 |
| 50 | 68.6 | 88.9 | 68.5 |
| 25 | 44.1 | 64.7 | 36.2 |
| 10 | 23.9 | 23.5 | 12.8 |
| 5 | 10.1 | 13.1 | 8.23 |
| 1 | 3.72 | 3.27 | 1.95 |

The inhibitory effects of 1,10-phenanthroline on the flavin-bound GDHs of the invention were as low as about 2-4% when 1,10-phenanthroline was added at 1 mM and about 10% even when 1,10-phenanthroline was added at 5 mM.

Example 4

Investigation 1 of the Quantitative Properties of Glucose Levels Using the Flavin-Bound GDHs Derived from *Mucor*

Glucose levels were measured using the above flavin-bound GDHs. Specifically, to initiate a reaction, 1.79 mL of 100 mM phosphate buffer (pH 7.0), 0.08 mL of D-glucose solution (250, 750, 1,250, 1,750, 2,500, 3,250, 4,000, and 5,000 mg/dL), and 0.01 mL of 20 mM DCIP solution were mixed, followed by incubation at 37° C. for five minutes, and 0.02 mL of 20 mM PMS solution and 0.1 mL of 0.8 U/mL GDH solution were added. The relationship between a decrease in the absorbance at 600 nm (ΔA600) per minute due to the progress of the enzyme reaction and the final concentration of glucose is shown in FIG. 7 (FIGS. 7 (A), (B), and (C) show the measurement results of MpGDH, MjGDH, and McGDH, respectively.).

Figure 7:
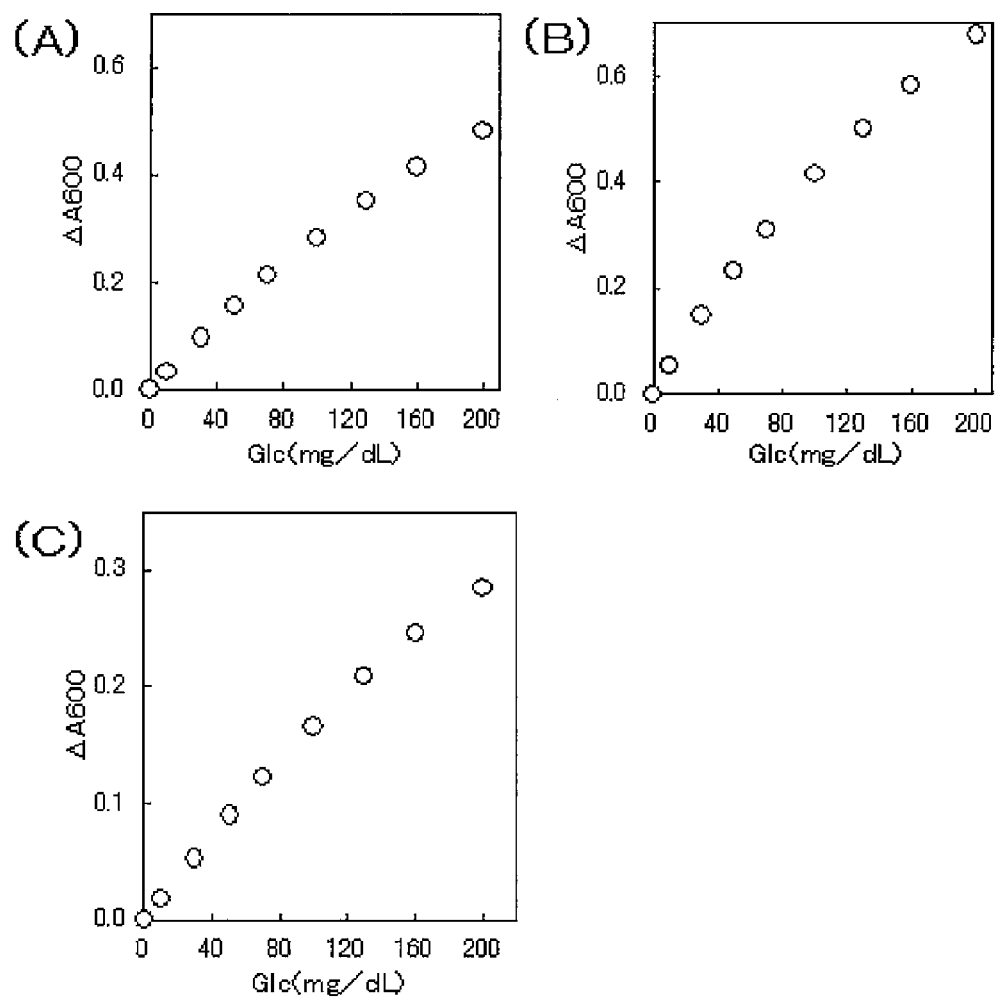
FIG. 7 Measurement of D-glucose using the flavin-bound GDHs used in the invention.

As shown in FIG. 7, it was demonstrated that glucose levels in measurement samples could be accurately measured at a final concentration of 200 mg/dL or below using the flavin-bound GDHs derived from *Mucor*.

Example 5

Investigation 2 of the Quantitative Properties of Glucose Levels Using the Flavin-Bound GDHs Derived from *Mucor*

To initiate a reaction, 1.77 mL of 100 mM phosphate buffer (pH 7.0), 0.02 mL of D-glucose solution (10,000 and 16,000 mg/dL), and 0.01 mL of 20 mM DCIP solution were mixed, and, subsequently, 0.08 mL of maltose solution (3,000, 6,000, 9,000, 12,000, and 15,000 mg/dL), D-galactose solution (1,500, 3,000, 4,500, 6,000, and 7,500 mg/dL), or D-xylose solution (1,000, 2,000, 3,000, 4,000, and 5,000 mg/dL) was added, followed by incubation at 37° C. for five minutes, and 0.02 mL of 20 mM PMS solution and 0.1 mL of 2.0 U/mL GDH solution were added. The relationship between a decrease in the absorbance at 600 nm (ΔA600) per minute due to the progress of the enzyme reaction and the final concentration of glucose is shown in Table 5-7.

TABLE 5

Comparison of glucose measurements in samples with the addition of various sugar compounds (Enzyme: MpGDH)

| | | | | | | |
|---|---|---|---|---|---|---|
| D-Glucose concentration (mg/dL) | | | 100 | | | |
| Maltose concentration (mg/dL) | 0 | 120 | 240 | 360 | 480 | 600 |
| ΔA600 | 0.394 | 0.393 | 0.398 | 0.398 | 0.399 | 0.401 |
| Relative value (%) | 100 | 100 | 101 | 101 | 101 | 102 |
| D-Glucose concentration (mg/dL) | | | 160 | | | |
| Maltose concentration (mg/dL) | 0 | 120 | 240 | 360 | 480 | 600 |
| ΔA600 | 0.534 | 0.535 | 0.540 | 0.540 | 0.542 | 0.535 |
| Relative value (%) | 100 | 100 | 101 | 101 | 102 | 100 |
| D-Glucose concentration (mg/dL) | | | 100 | | | |
| D-Galactose concentration (mg/dL) | 0 | 60 | 120 | 180 | 240 | 300 |
| ΔA600 | 0.394 | 0.392 | 0.393 | 0.393 | 0.393 | 0.394 |
| Relative value (%) | 100 | 100 | 100 | 100 | 100 | 100 |
| D-Glucose concentration (mg/dL) | | | 160 | | | |
| D-Galactose concentration (mg/dL) | 0 | 60 | 120 | 180 | 240 | 300 |
| ΔA600 | 0.534 | 0.513 | 0.530 | 0.535 | 0.529 | 0.533 |
| Relative value (%) | 100 | 96 | 99 | 100 | 99 | 100 |
| D-Glucose concentration (mg/dL) | | | 100 | | | |
| D-Xylose concentration (mg/dL) | 0 | 40 | 80 | 120 | 160 | 200 |
| ΔA600 | 0.394 | 0.388 | 0.390 | 0.389 | 0.386 | 0.386 |
| Relative value (%) | 100 | 100 | 99 | 99 | 98 | 98 |
| D-Glucose concentration (mg/dL) | | | 160 | | | |
| D-Xylose concentration (mg/dL) | 0 | 40 | 80 | 120 | 160 | 200 |
| ΔA600 | 0.534 | 0.530 | 0.529 | 0.525 | 0.527 | 0.522 |
| Relative value (%) | 100 | 99 | 99 | 98 | 99 | 98 |

TABLE 6

Comparison of glucose measurements in samples with the addition of various sugar compounds (Enzyme: MjGDH)

| | | | | | | |
|---|---|---|---|---|---|---|
| D-Glucose concentration (mg/dL) | | | 100 | | | |
| Maltose concentration (mg/dL) | 0 | 120 | 240 | 360 | 480 | 600 |
| ΔA600 | 0.857 | 0.861 | 0.867 | 0.864 | 0.871 | 0.868 |
| Relative value (%) | 100 | 101 | 101 | 101 | 102 | 101 |
| D-Glucose concentration (mg/dL) | | | 160 | | | |
| Maltose concentration (mg/dL) | 0 | 120 | 240 | 360 | 480 | 600 |
| ΔA600 | 1.222 | 1.230 | 1.222 | 1.234 | 1.228 | 1.238 |
| Relative value (%) | 100 | 101 | 100 | 101 | 101 | 101 |
| D-Glucose concentration (mg/dL) | | | 100 | | | |
| D-Galactose concentration (mg/dL) | 0 | 60 | 120 | 180 | 240 | 300 |
| ΔA600 | 0.857 | 0.863 | 0.864 | 0.865 | 0.863 | 0.854 |
| Relative value (%) | 100 | 101 | 101 | 101 | 101 | 100 |
| D-Glucose concentration (mg/dL) | | | 160 | | | |

TABLE 6-continued

Comparison of glucose measurements in samples with the addition of various sugar compounds (Enzyme: MjGDH)

| | | | | | | |
|---|---|---|---|---|---|---|
| D-Galactose concentration (mg/dL) | 0 | 60 | 120 | 180 | 240 | 300 |
| ΔA600 | 1.222 | 1.226 | 1.222 | 1.224 | 1.216 | 1.214 |
| Relative value (%) | 100 | 100 | 100 | 100 | 100 | 99 |
| D-Glucose concentration (mg/dL) | | | 100 | | | |
| D-Xylose concentration (mg/dL) | 0 | 40 | 80 | 120 | 160 | 200 |
| ΔA600 | 0.857 | 0.869 | 0.851 | 0.847 | 0.857 | 0.856 |
| Relative value (%) | 100 | 101 | 99 | 100 | 100 | 100 |
| D-Glucose concentration (mg/dL) | | | 160 | | | |
| D-Xylose concentration (mg/dL) | 0 | 40 | 80 | 120 | 160 | 200 |
| ΔA600 | 1.222 | 1.234 | 1.212 | 1.222 | 1.212 | 1.218 |
| Relative value (%) | 100 | 101 | 99 | 100 | 99 | 100 |

TABLE 7

Comparison of glucose measurements in samples with the addition of various sugar compounds (Enzyme: McGDH)

| | | | | | | |
|---|---|---|---|---|---|---|
| D-Glucose concentration (mg/dL) | | | 100 | | | |
| Maltose concentration (mg/dL) | 0 | 120 | 240 | 360 | 480 | 600 |
| ΔA600 | 0.431 | 0.434 | 0.443 | 0.444 | 0.443 | 0.444 |
| Relative value (%) | 100 | 101 | 103 | 103 | 103 | 103 |
| D-Glucose concentration (mg/dL) | | | 160 | | | |
| Maltose concentration (mg/dL) | 0 | 120 | 240 | 360 | 480 | 600 |
| ΔA600 | 0.637 | 0.646 | 0.649 | 0.654 | 0.652 | 0.653 |
| Relative value (%) | 100 | 101 | 102 | 103 | 102 | 103 |
| D-Glucose concentration (mg/dL) | | | 100 | | | |
| D-Galactose concentration (mg/dL) | 0 | 60 | 120 | 180 | 240 | 300 |
| ΔA600 | 0.431 | 0.437 | 0.438 | 0.439 | 0.443 | 0.441 |
| Relative value (%) | 100 | 101 | 102 | 102 | 103 | 102 |
| D-Glucose concentration (mg/dL) | | | 160 | | | |
| D-Galactose concentration (mg/dL) | 0 | 60 | 120 | 180 | 240 | 300 |
| ΔA600 | 0.637 | 0.644 | 0.646 | 0.639 | 0.645 | 0.640 |
| Relative value (%) | 100 | 101 | 101 | 100 | 101 | 101 |
| D-Glucose concentration (mg/dL) | | | 100 | | | |
| D-Xylose concentration (mg/dL) | 0 | 40 | 80 | 120 | 160 | 200 |
| ΔA600 | 0.431 | 0.439 | 0.440 | 0.443 | 0.442 | 0.435 |
| Relative value (%) | 100 | 102 | 102 | 103 | 103 | 101 |
| D-Glucose concentration (mg/dL) | | | 160 | | | |
| D-Xylose concentration (mg/dL) | 0 | 40 | 80 | 120 | 160 | 200 |
| ΔA600 | 0.637 | 0.644 | 0.645 | 0.643 | 0.646 | 0.642 |
| Relative value (%) | 100 | 101 | 101 | 101 | 101 | 101 |

As shown in Table 5-7, it was demonstrated that glucose levels in samples containing maltose at a final concentration of 600 mg/dL or below, D-galactose at a final concentration of 300 mg/dL or below, or D-xylose at a final concentration of 200 mg/dL or below could be accurately measured using these flavin-bound GDHs derived from *Mucor*.

Example 6

Investigation 3 of the Quantitative Properties of Glucose Levels Using the Flavin-Bound GDHs To initiate a reaction, 1.61 mL of 100 mM phosphate buffer (pH 7.0), 0.02 mL of D-glucose solution (10,000 and 16,000 mg/dL), and 0.01 mL of 20 mM DCIP solution were mixed, and, subsequently, 0.08 mL each of maltose solution (3,000, 6,000, 9,000, 12,000, and 15,000 mg/dL), D-galactose solution (1,500, 3,000, 4,500, 6,000, and 7,500 mg/dL), and D-xylose solution (1,000, 2,000, 3,000, 4,000, and 5,000 mg/dL) was added, followed by incubation at 37° C. for five minutes, and 0.02 mL of 20 mM PMS solution and 0.1 mL of 2.0 U/mL flavin-bound GDH solution were added. The relationship between a decrease in the absorbance at 600 nm (ΔA600) per minute due to the progress of the enzyme reaction and the final concentration of glucose is shown in Table 8-9.

TABLE 8

Comparison of glucose measurements in samples with the addition of three kinds of sugar compounds (Enzyme: MpGDH)

| | | | | | | |
|---|---|---|---|---|---|---|
| D-Glucose concentration (mg/dL) | | | 100 | | | |
| Maltose concentration (mg/dL) | 0 | 120 | 240 | 360 | 480 | 600 |
| D-Galactose concentration (mg/dL) | 0 | 60 | 120 | 180 | 240 | 300 |
| D-Xylose concentration (mg/dL) | 0 | 40 | 80 | 120 | 160 | 200 |
| ΔA600 | 0.637 | 0.640 | 0.644 | 0.650 | 0.652 | 0.647 |
| Relative value (%) | 100 | 101 | 101 | 102 | 102 | 102 |
| D-Glucose concentration (mg/dL) | | | 160 | | | |
| Maltose concentration (mg/dL) | 0 | 120 | 240 | 360 | 480 | 600 |
| D-Galactose concentration (mg/dL) | 0 | 60 | 120 | 180 | 240 | 300 |

TABLE 8-continued

Comparison of glucose measurements in samples with the addition of three kinds of sugar compounds (Enzyme: MpGDH)

| D-Xylose concentration (mg/dL) | 0 | 40 | 80 | 120 | 160 | 200 |
|---|---|---|---|---|---|---|
| ΔA600 | 0.726 | 0.747 | 0.750 | 0.750 | 0.748 | 0.755 |
| Relative value (%) | 100 | 103 | 103 | 103 | 103 | 104 |

TABLE 9

Comparison of glucose measurements in samples with the addition of three kinds of sugar compounds (Enzyme: MjGDH)

| D-Glucose concentration (mg/dL) | | | 100 | | | |
|---|---|---|---|---|---|---|
| Maltose concentration (mg/dL) | 0 | 120 | 240 | 360 | 480 | 600 |
| D-Galactose concentration (mg/dL) | 0 | 60 | 120 | 180 | 240 | 300 |
| D-Xylose concentration (mg/dL) | 0 | 40 | 80 | 120 | 160 | 200 |
| ΔA600 | 0.746 | 0.722 | 0.728 | 0.734 | 0.725 | 0.734 |
| Relative value (%) | 100 | 97 | 98 | 98 | 97 | 98 |
| D-Glucose concentration (mg/dL) | | | 160 | | | |
| Maltose concentration (mg/dL) | 0 | 120 | 240 | 360 | 480 | 600 |
| D-Galactose concentration (mg/dL) | 0 | 60 | 120 | 180 | 240 | 300 |
| D-Xylose concentration (mg/dL) | 0 | 40 | 80 | 120 | 160 | 200 |
| ΔA600 | 1.076 | 1.049 | 1.052 | 1.058 | 1.067 | 1.070 |
| Relative value (%) | 100 | 97 | 98 | 98 | 99 | 99 |

Table 8-9 demonstrate that MpGDH or MjGDH allows extremely accurate measurement of glucose levels in samples containing maltose at a final concentration of 600 mg/dL or below, D-galactose at a final concentration of 300 mg/dL or below, or D-xylose at a final concentration of 200 mg/dL or below.

Example 7

Cloning of a Flavin-Bound GDH Gene Derived from *Mucor* and Preparation of the Yeast Transformant (1) Preparation of mRNA

*Mucor prainii* NISL0103 was inoculated into 3 mL of malt extract medium (2.0% malt extract, 4.0% glucose, 0.1% polypeptone, pH 6.0), followed by shaking culture at 30° C. for 2 days. This culture medium was filtered through a filter paper to collect mycelia. The obtained mycelia were frozen in liquid nitrogen and homogenized using a mortar. Subsequently, mRNA was obtained from the homogenized mycelia using ISOGEN (Nippon Gene) according to the protocol of the kit.

(2) Determination of the Partial Amino Acid Sequence of GDH

The MpGDH obtained in Example 2 was subjected to SuperSep Ace 10-20% (Wako Pure Chemical Industries, Ltd.) and electrophoresed. The electrophoresed gel was stained using Quick-CBB (Wako Pure Chemical Industries, Ltd.). A band portion corresponding to the molecular weight of the enzyme was excised. The excised gel was outsourced to an outside agency to obtain the internal amino acid sequence information of the protein contained in the gel. The resulting amino acid sequences were LVENFTPPTPAQIE (SEQ ID NO: 5) and IRNSTDEWANYY (SEQ ID NO: 6).

(3) Determination of the GDH Gene Sequences

Degenerate primers containing mixed bases (exemplary primers are shown in SEQ ID NO: 7 (forward primer) and SEQ ID NO: 8 (reverse primer)) were prepared based on the above partial amino acid sequence information. In the single character codes of SEQ ID NO: 7 and 8, mixed bases are represented as h=a+c+t, r=a+g, y=c+t, and d=a+g+t. The mRNA of *Mucor prainii* NISL0103, prepared in the above (1), was used as a template to conduct RT-PCR using PrimeScript RT-PCR Kit (Takara Bio) according to the protocol of the kit. The oligo dT primer supplied with the kit was used for reverse transcription reaction. The degenerate primers of SEQ ID NO: 7 and 8 were used for cDNA amplification by PCR. The reaction solution was subjected to agarose gel electrophoresis. A single band corresponding to about 800-bp length was detected. The amplified DNA fragment contained in this band was purified and ligated to pT7Blue (Novagen) using Ligation Convenient Kit (Nippon Gene), constructing a recombinant plasmid, pTMGD-1.

Subsequently, the resulting pTMGD-1 was used to transform *E. coli* JM109 competent cells (Nippon Gene) by known heat shock method. Plasmids were extracted and purified from the resulting transformant using GenElute Plasmid Miniprep Kit (Sigma) to determine the base sequence of the amplified DNA fragment (767 bp) contained in the plasmids.

Based on the sequence information of the resulting amplified DNA fragment, the unknown 3' and 5' regions of the GDH gene were determined using 3'- and 5'-Full RACE Core Sets (Takara Bio), respectively. The 3-site adaptor-primer supplied with the kit and the primer of SEQ ID NO: 9 were used for 3'-Full RACE Core Set, while the primers of SEQ ID NO: 10, 11, 12, 13, and 14 were used for 5'-Full RACE Core Set, according to the protocols of the kits. The base sequences of the DNA fragments contained in the multiple plasmids obtained according to the above method were determined, revealing a GDH gene sequence with an entire length of 1,926 bp, derived from *Mucor prainii* NISL0103, as shown in SEQ ID NO: 2 and 4. The amino acid sequences of the enzyme gene, predicted from the gene sequences, are shown in SEQ ID NO: 1 and 3.

(4) Preparation and Culture of a Yeast Transformant and Detection of GDH Activity Double-joint PCR (Fungal Genetics and Biology, 2004, Volume 41, p973-981) was conducted to construct a gene expression cassette with 5'-arm region, URA5 gene (uracil auxotrophic marker), TDH1 promoter, GDH gene, and 3'-arm region tandemly linked. The 5'- and 3'-arm regions refer to about 1 kb regions upstream and downstream of the TDH1 gene of *Zygosaccharomyces rouxii* IFO1876, respectively. This was transformed into the competent cells of *Z. rouxii* IFO1876 by electroporation. The electroporation was conducted as reported in J Microbiol Methods 55 (2003)

481-484. The cells, thus obtained, are spread onto a minimal medium in a plate to obtain a yeast transformant using uracil non-requirement.

The yeast transformant of the invention with the above GDH gene expression cassette inserted and the control strain without insertion were inoculated into 1 ml of YPD liquid medium (2% Bacto-peptone, 1% Bacto-yeast extract, and 2% glucose) in a test tube, followed by pre-culture at 200 rpm at 30° C. for 24 hours. The preculture is inoculated at 1% (v/v) into 50 mL of YPD medium in a 300 mL-volume Erlenmeyer flask with baffles, followed by shaking culture at 200 rpm at 30° C. for 24 hours.

The resulting culture was transferred into a 50-ml Falcon tube, followed by centrifugation at 8,000×g at 4° C. for 5 minutes to separate cells and a supernatant. The GDH activities in the cells and the supernatant were determined. Specifically, the resulting cells were suspended in 50 mL of 10 mM acetate buffer (pH 5.0) and homogenized using a Multi-beads Shocker (Yasui Kikai) (2,000 rpm, 60 seconds, 8 times). The enzyme activity of the supernatant collected by centrifugation at 14,000×g for 10 minutes was determined as GDH activity inside of the cell. To remove components in the medium supernatant, the medium supernatant was subjected to a PD-10 column (GE Healthcare, Sweden) to determine the enzyme activity of a GDH fraction, obtained by elusion in 10 mM acetate buffer (pH 5.0), as GDH activity outside of the cell.

(5) GDH Production by the Yeast Transformant of the Invention

As a result of the above enzyme activity assay, the GDH activity inside of the cell was 4.6 U/mL, while that outside of the cell was 27.6 U/mL. Specifically, when the transformant of the invention was cultured, the GDH produced was mostly excreted into the culture supernatant. This demonstrates that the signal sequence, derived from *Mucor*, in the GDH of the invention also functions in the heterologous host, yeast, allowing more efficient GDH excretion into the culture supernatant than that achieved for the original microorganism.

In general, the functions of a signal peptide are often limited to a host producing the protein. A signal peptide effective in a certain host rarely exerts the same effects in heterologous hosts. Thus, the above results were completely unexpected effects.

As described above, GDH activity was detected at 27.6 U/mL in the culture supernatant of the yeast transformant of the invention at 24 hours after inoculation. This GDH exists in a high-purity form in the culture supernatant as almost a single band, allowing efficient purification. As listed in Table 1 of Example 1, the production levels of an enzyme obtained by culturing the original GDH-producing microorganism derived from *mucor* (e.g., *Mucor*, *Absidia*, and *Actinomucor*) were less than 0.001 U/mL, mostly 0.1-0.2 U/mL, and up to 0.714 U/mL. Specifically, the use of the yeast transformant of the invention provides a 40-200-fold or higher enzyme activity in culture medium and allows efficient production in smaller facilities. Furthermore, the culture process of these original GDH-producing microorganisms included long-term culture (3-5 days), cell homogenization after collecting cells by centrifugation (enzyme extraction), and preparation of a crude enzyme solution through second centrifugation. However, the use of the yeast transformant of the invention significantly shortens the culture time and reduces the burden of cell homogenization (enzyme extraction), allowing efficient GDH production.

Figure 8:
FIG. 8 SDS-polyacrylamide gel electrophoresis of the flavin-bound GDH produced by the yeast transformant of the invention.

(6) Molecular Weight and Glycosylation of the GDH Produced by the Yeast Transformant of the Invention The culture supernatant of the invention was 50-fold concentrated using Microcon YM-50 (Millipore, U.S.) and subjected to SDS-polyacrylamide electrophoresis (SuperSep Ace 10-20%, Wako Pure Chemical Industries, Ltd.). The electrophoresed samples are as follows. FIG. 8 shows the results.

Lane 1: Molecular weight marker (New England Biolabs, Inc., protein ladder (10-250 kDa), 250 kDa, 150 kDa, 100 kDa, 80 kDa, 60 kDa, 50 kDa, 40 kDa, and 30 kDa from the top)

Lane 2: Culture supernatant of the control strain (50-fold concentrated sample)

Lane 3: Culture supernatant of the yeast transformant of the invention (50-fold concentrated sample)

As shown in FIG. 8, a band undetectable in the culture supernatant of the control strain was detected in that of the yeast transformant of the invention. This band corresponds to the GDH of the invention, with a molecular weight of about 200 kDa, a broad single band ranging from about 150 to 250 kDa in the molecular weight from the top to the bottom of the band. Such broad band strongly suggests the addition of a large amount of sugar chains to this protein.

The GDH produced by *Mucor*, the original microorganism from which the GDH used in the invention derives, also shows such addition of sugar chains. As shown in FIG. 6, the molecular weight of the band to be detected changes before and after the removal of sugar chains from the GDH. The GDH derived from *Mucor* before the removal of sugar chains has a molecular weight of about 100-150 kDa, corresponding to the center of the band width, although it varies with the kinds of microorganisms. The MpGDH used for the yeast transformant described in Example 7 has a molecular weight of about 100 kDa. On the other hand, the GDH found in the culture supernatant of the yeast transformant of the invention, prepared using the genetic information of the MpGDH, has a molecular weight of about 200 kDa, corresponding to the center of the band width before the removal of sugar chains, suggesting an about 2-fold increase as compared with the expression in the original microorganism.

The specific addition state of sugar chains will be revealed in detail using various known analytical methods. As readily presumed from the above molecular weight changes, the use of the yeast transformant of the invention was demonstrated to allow the production of a novel GDH with a markedly different addition state of sugar chains, although the GDH has the same polypeptide sequence as the GDH derived from *Mucor*. The changes in the addition state of sugar chains in the GDH of the invention markedly changes the enzyme properties of GDH, providing a more practical GDH. This is a completely unexpected effect.

Figure 9:
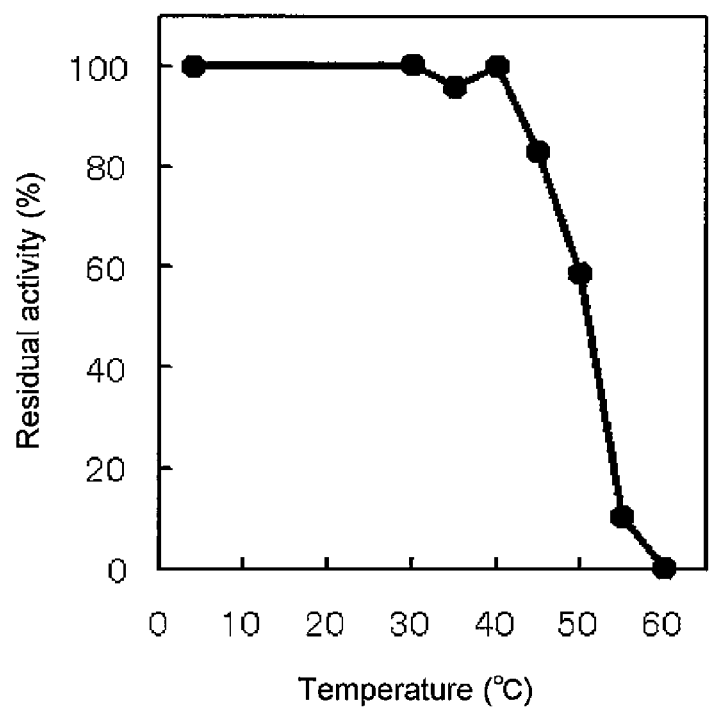
FIG. 9 Thermal stability of any one of the flavin-bound GDH produced by the yeast transformant of the invention.

(7) Various Properties of the GDHs Produced by the Yeast Transformant of the Invention According to Example 3, various properties, such as optimum pH, optimum temperature range, thermal stability, stable pH range, and substrate specificity, of the flavin-bound GDHs of the invention, obtained from the culture supernatant of the yeast transformant of the invention, were examined. As a result, the flavin-bound GDHs of the invention, produced by the yeast transformant of the invention, showed higher thermal stability than that of the GDH derived from *Mucor*. FIG. 9 shows the results.

As shown in FIG. 4, the GDHs produced by *Mucor*, an original microorganism, are barely inactivated at up to 35° C., and are characterized by having residual activity of 80% or above after treatment at 40° C. for 15 minutes. Then, the residual activity became 40-60% after treatment at 45° C. for 15 minutes. Two of three GDHs were completely inactivated when treated at 50° C. for 15 minutes. The activity of a GDH with the highest heat resistance was decreased to about 40%. All the GDHs were completely inactivated when heat-treated at 55° C. or above.

In contrast, as shown in FIG. 9, the flavin-bound GDHs of the invention, obtained from the culture supernatant of the yeast transformant of the invention, had almost 100% residual activity after treatment at 40° C. for 15 minutes. Furthermore, they had more than 80% residual activity even after treatment at 45° C. for 15 minutes and 50% or above or nearly 60% residual activity even after treatment at 50° C. for 15 minutes. Furthermore, the GDH produced by *Mucor* was completely inactivated after heat treatment for 15 minutes, but had about 10% residual activity even when subjected to heat treatment at 55° C. or above.

Figure 10:
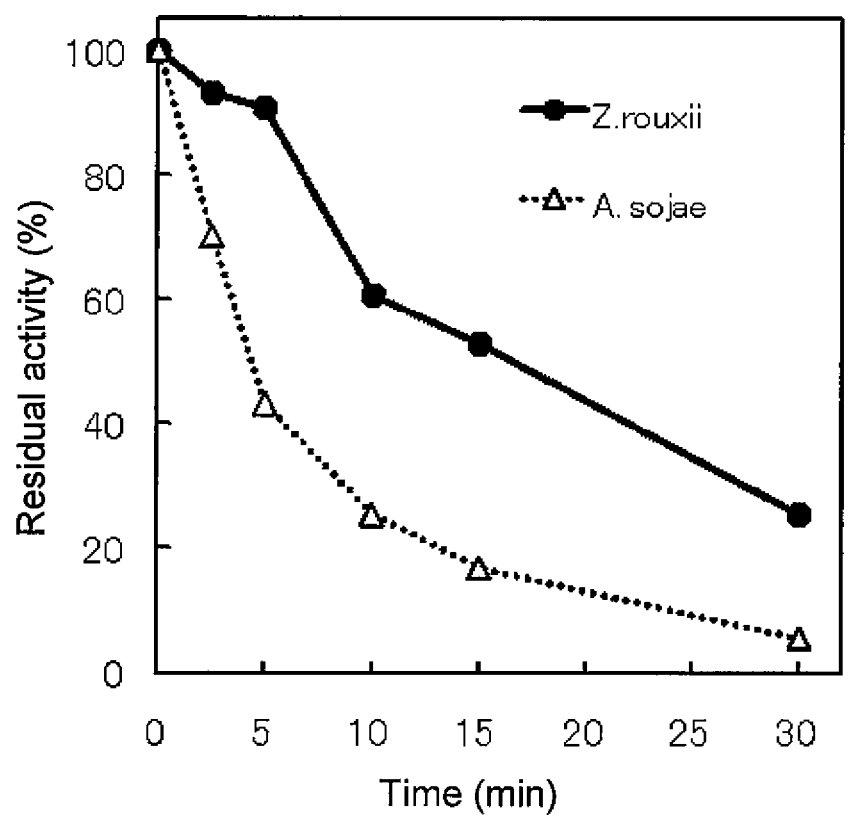
FIG. 10 A relationship between heat treatment time and residual activity, indicating the thermal stability of the flavin-bound GDH produced by the yeast transformant of the invention and the *Aspergillus* transformant of the comparative example.

The plots of black circles in FIG. 10 indicate the relationship between heat treatment time and residual activity when the GDH produced by the yeast transformant of the invention was subjected to heat treatment at 50° C. The results demonstrate that the GDH produced by the yeast transformant of the invention had 20% or above residual activity even after heat treatment at 50° C. for 30 minutes. The thermal stability of the GDH produced by the yeast transformant of the invention is significantly higher than that of the GDH produced by the original microorganism. Such high heat resistance, which could not be achieved by the original GDH produced by *Mucor*, could be achieved using the yeast transformant. This finding of the invention is very useful for manufacture and distribution. In addition, a novel useful enzyme can be provided to facilitate applications at a wide range of temperature, contributing to the added values of the GDHs.

The properties other than heat resistance of the flavin-bound GDH of the invention, obtained from the culture supernatant of the yeast transformant of the invention, were demonstrated to be similar to those of the purified GDH obtained in Example 2.

(8) Comparison of the Heat Resistance of the GDHs Produced by the Transformant Generated by Using *Aspergillus* as a Host Transformants were prepared using hosts other than yeast of the invention to compare the heat resistance of the resulting GDHs. *Aspergillus*, the same kind of fungus as the original microorganism, was used as a host for comparison.

Specifically, double-joint PCR (Fungal Genetics and Biology, 2004, Volume 41, p973-981) was conducted to construct a cassette consisting of 5'-arm region, PyrG gene (uracil auxotrophic marker), TEF1 promoter, flavin-bound GDH gene, and 3'-arm region. The cassette was transformed into *Aspergillus sojae* K. K. 1-2 strain as a host using protoplast-PEG method. Among the resulting strains, an *Aspergillus* transformant of interest was selected by PCR.

Subsequently, 5 g of wheat bran was dispersed in water at 0.8% in a 150-mL Erlenmeyer flask. The flask was cotton-plugged, followed by autoclave sterilization at 121° C. for 50 minutes. The conidium suspension of the above *Aspergillus* transformant was inoculated at $1 \times 10^5$/g koji and cultured at 30° C. for 64 hours. A nontransformed *Aspergillus* host was used as a control strain.

To 2 g of bran koji after culture, five volumes of 10 mM acetate buffer (pH 5.0) were added, followed by homogenization for 30 seconds eight times using a Polytron PT3000 homogenizer (Kinematica). After the homogenization, the homogenate was centrifuged at 14,000 rpm for 30 minutes. The resulting supernatant fraction was used as a crude enzyme solution. The GDH activities in these crude enzyme solutions were measured by the above enzyme activity assay. The GDH activity in the crude enzyme solution obtained using the control strain was 0.3 U/mL, while that in the crude enzyme solution obtained using the *Aspergillus* transformant was 14.0 U/mL, demonstrating that the flavin-bound GDH of the invention was expressed in the *Aspergillus* transformant.

Figure 11:
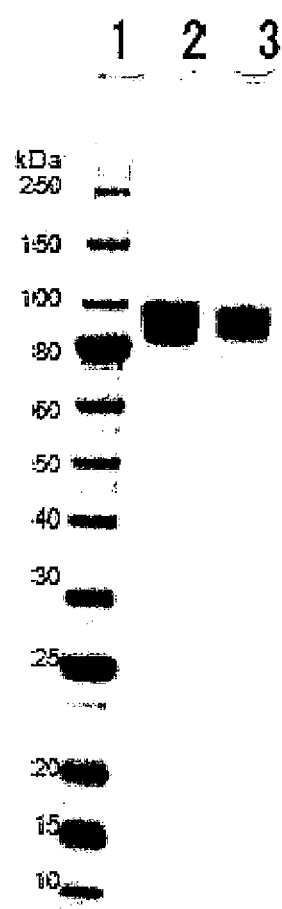
FIG. 11 SDS-polyacrylamide gel electrophoresis of the flavin-bound GDHs derived from *Mucor*, produced by the *Aspergillus* transformants of the comparative example.

The purified flavin-bound GDH derived from *Mucor*, produced by the above *Aspergillus* transformant obtained according to Example 2, was subjected to SDS-polyacrylamide electrophoresis according to the above method (6). The electrophoresed samples are as follows. FIG. 11 shows the results. The samples in Lanes 2 and 3 are GDHs produced by different transformants.
Lane 1: Molecular weight marker (New England Biolabs, Inc., protein ladder (10-250 kDa), 250 kDa, 150 kDa, 100 kDa, 80 kDa, 60 kDa, 50 kDa, 40 kDa, and 30 kDa from the top)
Lanes 2 and 3: GDHs produced by the *Aspergillus* transformant obtained As shown in FIG. 10, this band corresponds to the GDH derived from *Mucor*, produced by the *Aspergillus* transformant of the invention, with a molecular weight of about 90 kDa, a broad single band ranging from about 80 to 100 kDa in the molecular weight from the top to the bottom of the band.

A comparison of the bands among FIGS. 6, 8, and 11 demonstrates that the molecular weight of the GDH derived from *Mucor*, produced by the *Aspergillus* transformant, was very close to that of the GDH produced by *Mucor*, the original microorganism and was significantly different from that of the GDH derived from *Mucor*, produced by the yeast transformant of the invention. Specifically, these results strongly suggested that the addition state of sugar chains in the GDH derived from *Mucor*, produced by the *Aspergillus* transformant, was close to that in the GDH produced by *Mucor*, the original microorganism and was significantly different from that of the GDH derived from *Mucor*, produced by the yeast transformant of the invention.

FIG. 10 shows the heat resistance data of the GDH derived from *Mucor* actually produced by the *Aspergillus* transformant. The plots of white triangles in FIG. 10 indicate the relationship between heat treatment time and residual activity when the GDH produced by the *Aspergillus* transformant was subjected to heat treatment at 50° C. As a result, the residual activity of the GDH produced by the *Aspergillus* transformant was decreased to less than 20% by heat treatment at 50° C. for 15 minutes. The residual activity was decreased to less than 10% by treatment for 30 minutes. The thermal stability seemed to be decreased as compared with the GDH produced by the original microorganism.

Specifically, when the GDH gene derived from *Mucor* is introduced into various hosts, the activity cannot necessarily be expressed with its original enzyme properties maintained and, furthermore, the activity cannot readily be expressed as an enzyme with more excellent properties than the original enzyme. This could be achieved using the yeast transformant. This finding of the invention is very useful for manufacture and distribution. In addition, a novel useful enzyme can be provided to facilitate applications in a wider range of temperature, contributing to the added values of the GDHs.

The thermal stability of the GDH derived from *Mucor*, produced by the *Aspergillus* transformant, was relatively closer to that of the GDH produced by *Mucor*, the original microorganism, as shown in FIG. 6, than that of the GDH derived from *Mucor*, produced by the yeast transformant of the invention. These results suggest a correlation between the addition of sugar chains and thermal stability in the GDHs. Specifically, it was presumed that the GDHs produced by the yeast transformant of the invention have sugar chains added in a large amount and, thus, achieved higher heat resistance than that produced by *Mucor*, the original microorganism.

INDUSTRIAL APPLICABILITY

A heat-resistant flavin-bound glucose dehydrogenase that is less susceptible to the effects of dissolved oxygen and allows accurate measurement of glucose even in the presence of sugar compounds other than glucose in a sample can be efficiently produced.

The invention claimed is:

1. A flavin-bound glucose dehydrogenase having the amino acid sequence of SEQ ID NO: 3, and having the following properties (i) to (iv):
   (i) action: glucose dehydrogenase activity in the presence of an electron acceptor;
   (ii) molecular weight: the molecular weight of the polypeptide chain portion of the protein is approximately 80 kDa;
   (iii) substrate specificity: lower reactivity to maltose, D-galactose, and D-xylose than that to D-glucose; and
   (iv) 50% or above residual activity after heat treatment at 50° C. for 15 minutes, wherein the flavin-bound glucose dehydrogenase is produced by a yeast transformant.

2. A flavin-bound glucose dehydrogenase having an amino acid sequence having at least 85% sequence identity to SEQ ID NO: 3, and having the following properties (i) to (iv):

(i) action: glucose dehydrogenase activity in the presence of an electron acceptor;
(ii) molecular weight: the molecular weight of the polypeptide chain portion of the protein is approximately 80 kDa;
(iii) substrate specificity: lower reactivity to maltose, D-galactose, and D-xylose than that to D-glucose; and
(iv) 50% or above residual activity after heat treatment at 50° C. for 15 minutes, wherein the flavin-bound glucose dehydrogenase is produced by a yeast transformant.

3. The flavin-bound glucose dehydrogenase of claim 1, wherein said flavin-bound glucose dehydrogenase is obtained from a microorganism classified as Mucoromycotina.

4. The flavin-bound glucose dehydrogenase of claim 2, wherein said flavin-bound glucose dehydrogenase is obtained from a microorganism classified as Mucoromycotina.

5. The flavin-bound glucose dehydrogenase of claim 1, wherein said glucose dehydrogenase is obtained from a microorganism classified as Mucoromycetes.

6. The flavin-bound glucose dehydrogenase of claim 1, wherein said glucose dehydrogenase is obtained from a microorganism classified as Mucorales.

7. The flavin-bound glucose dehydrogenase of claim 1, wherein said glucose dehydrogenase is obtained from a microorganism classified as Mucoraceae.

8. The flavin-bound glucose dehydrogenase of claim 2, wherein said glucose dehydrogenase is obtained from a microorganism classified as Mucoromycetes.

9. The flavin-bound glucose dehydrogenase of claim 2, wherein said glucose dehydrogenase is obtained from a microorganism classified as Mucorales.

10. The flavin-bound glucose dehydrogenase of claim 2, wherein said glucose dehydrogenase is obtained from a microorganism classified as Mucoraceae.

* * * * *

SEQUENCE LISTING

```
<160> NUMBER OF SEQ ID NOS: 14

<210> SEQ ID NO 1
<211> LENGTH: 641
<212> TYPE: PRT
<213> ORGANISM: Mucor prainii

<400> SEQUENCE: 1

Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Ser Thr Asp Thr Tyr
                20                  25                  30

Asp Tyr Val Thr Val Gly Gly Gly Val Ala Gly Leu Ala Leu Ala Ser
            35                  40                  45

Arg Ile Ser Glu Asn Lys Asp Val Thr Val Ala Val Leu Glu Ser Gly
    50                  55                  60

Pro Asn Ala Asn Asp Arg Phe Val Val Tyr Ala Pro Gly Met Tyr Gly
65                  70                  75                  80

Gln Ala Val Gly Thr Asp Leu Cys Pro Leu Ile Pro Thr Thr Pro Gln
                85                  90                  95

Glu Asn Met Gly Asn Arg Ser Leu Thr Ile Ala Thr Gly Arg Leu Leu
                100                 105                 110

Gly Gly Gly Ser Ala Ile Asn Gly Leu Val Trp Thr Arg Gly Gly Leu
            115                 120                 125

Lys Asp Tyr Asp Ala Trp Glu Glu Leu Gly Asn Pro Gly Trp Asn Gly
    130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Ala His
                165                 170                 175

Gly Lys Lys Gly Pro Ile Asp Val Ser Phe Thr Asn Tyr Glu Phe Ser
                180                 185                 190

Gln Ser Ala Ser Trp Asn Ala Ser Leu Glu Thr Leu Asp Phe Thr Ala
            195                 200                 205

Leu Pro Asp Ile Leu Asn Gly Thr Leu Ala Gly Tyr Ser Thr Thr Pro
    210                 215                 220

Asn Ile Leu Asp Pro Glu Thr Val Gln Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255

His Thr Val Ser Arg Ile Gln Phe Ala Pro Lys Asn Gly Ser Glu Pro
                260                 265                 270

Leu Lys Ala Thr Gly Val Glu Trp Tyr Pro Thr Gly Asn Lys Asn Gln
            275                 280                 285

Lys Gln Ile Ile Lys Ala Arg Tyr Glu Val Ile Ile Ser Ser Gly Ala
        290                 295                 300
```

Ile Gly Ser Pro Lys Leu Leu Glu Ile Ser Gly Ile Gly Asn Lys Asp
305                 310                 315                 320

Ile Val Ser Ala Ala Gly Val Glu Ser Leu Ile Asp Leu Pro Gly Val
            325                 330                 335

Gly Ser Asn Met Gln Asp His Val His Ala Ile Thr Val Ser Thr Thr
        340                 345                 350

Asn Ile Thr Gly Tyr Thr Thr Asn Ser Val Phe Val Asn Glu Thr Leu
    355                 360                 365

Ala Gln Glu Gln Arg Glu Gly Tyr Glu Ala Asn Lys Thr Gly Ile Trp
370                 375                 380

Ala Thr Thr Pro Asn Asn Leu Gly Tyr Pro Thr Pro Glu Gln Leu Phe
385                 390                 395                 400

Asn Gly Thr Glu Phe Val Ser Gly Lys Glu Phe Ala Asp Lys Ile Arg
            405                 410                 415

Asn Ser Thr Asp Glu Trp Ala Asn Tyr Tyr Ala Ser Thr Asn Ala Ser
        420                 425                 430

Asn Val Glu Leu Leu Lys Lys Gln Tyr Ala Ile Val Ala Ser Arg Tyr
    435                 440                 445

Glu Glu Asn Tyr Leu Ser Pro Ile Glu Ile Asn Phe Thr Pro Gly Tyr
450                 455                 460

Glu Gly Ser Gly Asn Val Asp Leu Gln Asn Asn Lys Tyr Gln Thr Val
465                 470                 475                 480

Asn His Val Leu Ile Ala Pro Leu Ser Arg Gly Tyr Thr His Ile Asn
            485                 490                 495

Ser Ser Asp Val Glu Asp His Ser Val Ile Asn Pro Gln Tyr Tyr Ser
        500                 505                 510

His Pro Met Asp Ile Asp Val His Ile Ala Ser Thr Lys Leu Ala Arg
    515                 520                 525

Glu Ile Ile Thr Ala Ser Pro Gly Leu Gly Asp Ile Asn Ser Gly Glu
530                 535                 540

Ile Glu Pro Gly Met Asn Ile Thr Ser Glu Asp Asp Leu Arg Ser Trp
545                 550                 555                 560

Leu Ser Asn Asn Val Arg Ser Asp Trp His Pro Val Gly Thr Cys Ala
            565                 570                 575

Met Leu Pro Lys Glu Leu Gly Gly Val Val Ser Pro Ala Leu Met Val
        580                 585                 590

Tyr Gly Thr Ser Asn Leu Arg Val Val Asp Ala Ser Ile Met Pro Leu
    595                 600                 605

Glu Val Ser Ser His Leu Met Gln Pro Thr Tyr Gly Ile Ala Glu Lys
610                 615                 620

Ala Ala Asp Ile Ile Lys Asn Phe Tyr Lys Thr Gln His Lys Asn Gln
625                 630                 635                 640

Asn

<210> SEQ ID NO 2
<211> LENGTH: 1926
<212> TYPE: DNA
<213> ORGANISM: Mucor prainii

<400> SEQUENCE: 2
atgaagatca cagctgccat tatcactgtt gccacagcat ttgcttcttt tgcttctgct      60
caacaagaca caaattcttc ctcaactgat acttatgatt atgttaccgt tggcggcggt     120
gtagctggtt tggctttggc tagtcgtatc tctgaaaaca aggatgtcac tgttgctgtt     180

```
ctcgagtccg gtcctaatgc caatgataga tttgttgttt atgctcctgg catgtatggc    240
caagctgttg gcactgatct ctgtcctctc attcctacta ctcctcaaga aaatatgggc    300
aacagaagtc tcacaatcgc tactggtaga ttgctcggtg gtggcagtgc tattaatggt    360
ctcgtttgga cccgtggtgg cttgaaggat tacgatgctt gggaggagct cggtaaccct    420
ggatggaacg gtgccaactt gttcaagtac tttaagaagg tcgaaaactt cactcctcct    480
actcctgcac aaattgaata cggcgctact tatcagaaaa gtgctcatgg caagaaggga    540
cctattgatg tctctttcac gaactacgag ttctctcaat ctgctagctg aacgcctca    600
ctcgaaaccc ttgatttcac tgcacttcct gatatcttga acggtacttt ggccggttac    660
tctaccactc ccaacatttt ggaccctgag actgttcaac gtgttgattc ctatactggt    720
tacattgctc cttacactag ccgtaacaac ctcaatgttt tggccaacca taccgtctcc    780
cgcattcaat tgctcccaa gaatggtagc gaacctctca aggctaccgg tgttgaatgg    840
tatcccactg gcaacaagaa tcaaaagcaa attatcaagg cccgttatga agttatcatc    900
tcatctggtg ccattggtag tcctaagctt ttggaaatct ctggtatcgg taataaggat    960
atcgtctctg ctgctggtgt cgagtccttg attgacttgc ctggcgttgg ttccaacatg   1020
caagatcacg ttcatgctat cactgtctct actaccaata ttactggcta tactaccaac   1080
agcgtctttg tcaatgaaac ccttgcccaa gaacaaagag aagaatatga agccaacaag   1140
actggtatct gggctactac tcccaacaac ctcggttatc ctacgcccga caactcttc    1200
aatggcaccg aattcgtttc tggaaaggag tttgctgaca agattcgtaa ctctactgat   1260
gaatgggcca actattatgc ttccaccaac gcctccaatg tcgagttatt aaagaagcaa   1320
tatgctattg tcgcctctcg ttacgaagag aactacttgt ctcctattga aatcaacttc   1380
actcctggtt atgagggtag cggtaatgtc gatttgcaaa acaacaagta ccaaactgtc   1440
aaccatgtct tgattgctcc tttaagtcgt ggttatactc acattaactc ttctgatgtg   1500
gaggatcatt ctgtcattaa tccccaatac tactctcatc ctatggatat tgatgtccat   1560
atcgcttcca ctaaacttgc tcgcaaatc atcactgcct ctcccggtct tggtgacatt   1620
aacagtggcg aaatcgaacc cggtatgaat attacttctg aagacgacct tagatcttgg   1680
ttgagtaata atgtccgttc tgactggcat cctgttggta cttgtgctat gcttcccaag   1740
gaattaggtg gtgttgtcag ccccgctctc atggtttacg gcacttccaa cttgcgtgtt   1800
gttgatgctt cgattatgcc cctcgaagtc tcttctcatt tgatgcaacc cacctacggt   1860
attgctgaga aggctgctga cattattaag aatttctaca agactcaaca caagaaccaa   1920
aattag                                                              1926
```

<210> SEQ ID NO 3
<211> LENGTH: 641
<212> TYPE: PRT
<213> ORGANISM: Mucor prainii

<400> SEQUENCE: 3

```
Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Thr Asp Thr Tyr
            20                  25                  30

Asp Tyr Val Ile Val Gly Gly Gly Val Ala Gly Leu Ala Leu Ala Ser
        35                  40                  45

Arg Ile Ser Glu Asn Lys Asp Val Thr Val Ala Val Leu Glu Ser Gly
```

```
                50                  55                  60
Pro Asn Ala Asn Asp Arg Phe Val Val Tyr Ala Pro Gly Met Tyr Gly
65                  70                  75                  80

Gln Ala Val Gly Thr Asp Leu Cys Pro Leu Ile Pro Thr Thr Pro Gln
                85                  90                  95

Glu Asn Met Gly Asn Arg Ser Leu Thr Ile Ala Thr Gly Arg Leu Leu
                100                 105                 110

Gly Gly Gly Ser Ala Ile Asn Gly Leu Val Trp Thr Arg Gly Gly Leu
                115                 120                 125

Lys Asp Tyr Asp Ala Trp Glu Glu Leu Gly Asn Pro Gly Trp Asn Gly
                130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Ala His
                165                 170                 175

Gly Lys Lys Gly Pro Ile Asp Val Ser Phe Thr Asn Tyr Glu Phe Ser
                180                 185                 190

Gln Ser Ala Ser Trp Asn Ala Ser Leu Glu Thr Leu Asp Phe Thr Ala
                195                 200                 205

Leu Pro Asp Ile Leu Asn Gly Thr Leu Ala Gly Tyr Ser Thr Thr Pro
210                 215                 220

Asn Ile Leu Asp Pro Glu Thr Val Gln Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255

His Thr Val Ser Arg Ile Gln Phe Ala Pro Lys Asn Gly Ser Glu Pro
                260                 265                 270

Leu Lys Ala Thr Gly Val Glu Trp Tyr Pro Thr Gly Asn Lys Asn Gln
                275                 280                 285

Lys Gln Ile Ile Lys Ala Arg Tyr Glu Val Ile Ile Ser Ser Gly Ala
                290                 295                 300

Ile Gly Ser Pro Lys Leu Leu Glu Ile Ser Gly Ile Gly Asn Lys Asp
305                 310                 315                 320

Ile Val Ser Ala Ala Gly Val Glu Ser Leu Ile Asp Leu Pro Gly Val
                325                 330                 335

Gly Ser Asn Met Gln Asp His Val His Ala Ile Thr Val Ser Thr Thr
                340                 345                 350

Asn Ile Thr Gly Tyr Thr Thr Asn Ser Val Phe Val Asn Glu Thr Leu
                355                 360                 365

Ala Gln Glu Gln Arg Glu Glu Tyr Glu Ala Asn Lys Thr Gly Ile Trp
                370                 375                 380

Ala Thr Thr Pro Asn Asn Leu Gly Tyr Pro Thr Pro Glu Gln Leu Phe
385                 390                 395                 400

Asn Gly Thr Glu Phe Val Ser Gly Lys Glu Phe Ala Asp Lys Ile Arg
                405                 410                 415

Asn Ser Thr Asp Glu Trp Ala Asn Tyr Tyr Ala Ser Thr Asn Ala Ser
                420                 425                 430

Asn Val Glu Leu Leu Lys Lys Gln Tyr Ala Ile Val Ala Ser Arg Tyr
                435                 440                 445

Glu Glu Asn Tyr Leu Ser Pro Ile Glu Ile Asn Phe Thr Pro Gly Tyr
                450                 455                 460

Glu Gly Ser Gly Asn Val Asp Leu Gln Asn Asn Lys Tyr Gln Thr Val
465                 470                 475                 480
```

```
Asn His Val Leu Ile Ala Pro Leu Ser Arg Gly Tyr Thr His Ile Asn
                485                 490                 495

Ser Ser Asp Val Glu Asp His Ser Val Ile Asn Pro Gln Tyr Tyr Ser
            500                 505                 510

His Pro Met Asp Ile Asp Val His Ile Ala Ser Thr Lys Leu Ala Arg
        515                 520                 525

Glu Ile Ile Thr Ala Ser Pro Gly Leu Gly Asp Ile Asn Ser Gly Glu
    530                 535                 540

Ile Glu Pro Gly Met Asn Ile Thr Ser Glu Asp Asp Leu Arg Ser Trp
545                 550                 555                 560

Leu Ser Asn Asn Val Arg Ser Asp Trp His Pro Val Gly Thr Cys Ala
                565                 570                 575

Met Leu Pro Lys Glu Leu Gly Gly Val Val Ser Pro Ala Leu Met Val
            580                 585                 590

Tyr Gly Thr Ser Asn Leu Arg Val Val Asp Ala Ser Ile Met Pro Leu
        595                 600                 605

Glu Val Ser Ser His Leu Met Gln Pro Thr Tyr Gly Ile Ala Glu Lys
    610                 615                 620

Ala Ala Asp Ile Ile Lys Asn Phe Tyr Lys Thr Gln His Lys Asn Gln
625                 630                 635                 640

Asn

<210> SEQ ID NO 4
<211> LENGTH: 1926
<212> TYPE: DNA
<213> ORGANISM: Mucor prainii

<400> SEQUENCE: 4
atgaagatca cagctgccat tatcactgtt gccacagcat ttgcttcttt tgcttctgct    60
caacaagaca caaattcttc ctcaactgat acttatgatt atgttatcgt tggcggcgtt   120
gtagctggtt tggctttggc tagtcgtatc tctgaaaaca aggatgtcac tgttgctgtt   180
ctcgagtccg gtcctaatgc caatgataga tttgttgttt atgctcctgg catgtatggc   240
caagctgttg gcactgatct ctgtcctctc attcctacta ctcctcaaga aaatatgggc   300
aacagaagtc tcacaatcgc tactggtaga ttgctcggtg gtggcagtgc tattaatggt   360 ctcgttttgga cccgtggtgg cttgaaggat tacgatgctt gggaggagct cggtaaccct   420
ggatggaacg gtgccaactt gttcaagtac tttaagaagg tcgaaaactt cactcctcct   480
actcctgccc aaattgaata cggcgctact tatcagaaaa gtgctcatgg caagaaggga   540
cctattgatg tctctttcac gaactacgag ttctctcaat ctgctagctg aacgcctca   600 ctcgaaaccc ttgatttcac tgcacttcct gatatcttga acggtacttt ggccggttac   660
tctaccactc ccaacatttt ggaccctgag actgttcaac gtgttgattc ctatactggt   720
tacattgctc cttacactag ccgtaacaac ctcaatgttt tggccaacca taccgtctcc   780
cgcattcaat ttgctcccaa gaatggtagc gaacctctca aggctaccgg tgttgaatgg   840
tatcccactg caacaagaa tcaaaagcaa attatcaagg cccgttatga agttatcatc   900
tcatctggtg ccattggtag tcctaagctt ttggaaatct ctggtatcgg taataaggat   960
atcgtctctg ctgctggtgt cgagtccttg attgacttgc tggcgttgg ttccaacatg  1020 caagatcacg ttcatgctat cactgtctct actaccaata ttactggcta ctactaccaac  1080 agcgtctttg tcaatgaaac ccttgcccaa gaacaaagag aagaatatga agccaacaag  1140
```

-continued

| | |
|---|---|
| actggtatct gggctactac tcccaacaac ctcggttatc ctacgcccga caactcttc | 1200 |
| aatggcaccg aattcgtttc tggaaaggag tttgctgaca agattcgtaa ctctactgat | 1260 |
| gaatgggcca actattatgc ttccaccaac gcctccaatg tcgagttatt aaagaagcaa | 1320 |
| tatgctattg tcgcctctcg ttacgaagag aactacttgt ctcctattga aatcaacttc | 1380 |
| actcctggtt atgagggtag cggtaatgtc gatttgcaaa acaacaagta ccaaactgtc | 1440 |
| aaccatgtct tgattgctcc tttaagtcgt ggttatactc acattaactc ttctgatgtg | 1500 |
| gaggatcatt ctgtcattaa tccccaatac tactctcatc ctatggatat tgatgtccat | 1560 |
| atcgcttcca ctaaacttgc tcgcgaaatc atcactgcct ctcccggtct tggtgacatt | 1620 |
| aacagtggcg aaatcgaacc cggtatgaat attacttctg aagacgacct tagatcttgg | 1680 |
| ttgagtaata atgtccgttc tgactggcat cctgttggta cttgtgctat gcttcccaag | 1740 |
| gaattaggtg gtgttgtcag ccccgctctc atggtttacg gcacttccaa cttgcgtgtt | 1800 |
| gttgatgctt cgattatgcc cctcgaagtc tcttctcatt tgatgcaacc cacctacggt | 1860 |
| attgctgaga aggctgctga cattattaag aatttctaca agactcaaca caagaaccaa | 1920 |
| aattag | 1926 |

<210> SEQ ID NO 5
<211> LENGTH: 14
<212> TYPE: PRT
<213> ORGANISM: Mucor prainii

<400> SEQUENCE: 5

Leu Val Glu Asn Phe Thr Pro Pro Thr Pro Ala Gln Ile Glu
1               5                   10

<210> SEQ ID NO 6
<211> LENGTH: 12
<212> TYPE: PRT
<213> ORGANISM: Mucor prainii

<400> SEQUENCE: 6

Ile Arg Asn Ser Thr Asp Glu Trp Ala Asn Tyr Tyr
1               5                   10

<210> SEQ ID NO 7
<211> LENGTH: 21
<212> TYPE: DNA
<213> ORGANISM: Artificial
<220> FEATURE:
<223> OTHER INFORMATION: primer 1 (forward)

<400> SEQUENCE: 7
cchachcchg chcaratyga r                                          21

<210> SEQ ID NO 8
<211> LENGTH: 24
<212> TYPE: DNA
<213> ORGANISM: Artificial
<220> FEATURE:
<223> OTHER INFORMATION: primer 2 (reverse)

<400> SEQUENCE: 8
rtartarttd gcccaytcrt cdgt                                       24

<210> SEQ ID NO 9
<211> LENGTH: 24
<212> TYPE: DNA
<213> ORGANISM: Artificial

```
<220> FEATURE:
<223> OTHER INFORMATION: primer 3 for 3'-RACE

<400> SEQUENCE: 9
cctacacctg cacaaattga atac                                            24

<210> SEQ ID NO 10
<211> LENGTH: 14
<212> TYPE: DNA
<213> ORGANISM: Artificial
<220> FEATURE:
<223> OTHER INFORMATION: primer 4 for 5'-RACE

<400> SEQUENCE: 10
ggcgttccag ctag                                                       14

<210> SEQ ID NO 11
<211> LENGTH: 20
<212> TYPE: DNA
<213> ORGANISM: Artificial
<220> FEATURE:
<223> OTHER INFORMATION: primer 5 for 5'-RACE

<400> SEQUENCE: 11
caagaaggga cctattgatg                                                 20

<210> SEQ ID NO 12
<211> LENGTH: 22
<212> TYPE: DNA
<213> ORGANISM: Artificial
<220> FEATURE:
<223> OTHER INFORMATION: primer 6 for 5'-RACE

<400> SEQUENCE: 12
gagcactttt ctgataagta gc                                              22

<210> SEQ ID NO 13
<211> LENGTH: 22
<212> TYPE: DNA
<213> ORGANISM: Artificial
<220> FEATURE:
<223> OTHER INFORMATION: primer 7 for 5'-RACE

<400> SEQUENCE: 13
cgaactacga gttctctcaa tc                                              22

<210> SEQ ID NO 14
<211> LENGTH: 21
<212> TYPE: DNA
<213> ORGANISM: Artificial
<220> FEATURE:
<223> OTHER INFORMATION: primer 8 for 5'-RACE

<400> SEQUENCE: 14
cgtattcaat ttgtgcaggt g                                               21
```